(12) United States Patent
Buchsbaum et al.

(10) Patent No.: US 6,599,909 B1
(45) Date of Patent: Jul. 29, 2003

(54) MOLECULAR CHEMOTHERAPY ENHANCEMENT OF RADIOTHERAPY

(75) Inventors: Donald J. Buchsbaum, Birmingham, AL (US); David T. Curiel, Birmingham, AL (US); Murray A. Stackhouse, Birmingham, AL (US); Lee C. Pederson, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/408,055

(22) Filed: Sep. 29, 1999

Related U.S. Application Data

(60) Provisional application No. 60/102,391, filed on Sep. 29, 1998.

(51) Int. Cl.[7] .................. A61K 31/505; A61K 48/00
(52) U.S. Cl. ...................................... 514/274; 424/93.21
(58) Field of Search ........................ 514/274; 424/93.21

(56) References Cited

PUBLICATIONS

Pederson et al., Cancer Res., (1997), 57(19), 4325–4332.*

* cited by examiner

Primary Examiner—Jerome D Goldberg
(74) Attorney, Agent, or Firm—Benjamin Aaron Adler

(57) ABSTRACT

The present invention provides a new approach for cancer treatment by utilizing gene therapy combined with radiation therapy to enhance cytotoxicity in malignant cells. Specifically, the present invention demonstrates that molecular chemotherapy with the cytosine deaminase gene and 5-fluorocytosine is an effective radiosensitizing strategy which may lead to substantial improvement in tumor control, with less normal tissue toxicity than conventional systemic administration of 5-fluorouracil, that would translate into improved cure rates and better survival. Also provided is a noninvasive method for continuous in vivo monitoring of 5-fluorouracil production via magnetic resonance spectroscopy.

7 Claims, 22 Drawing Sheets

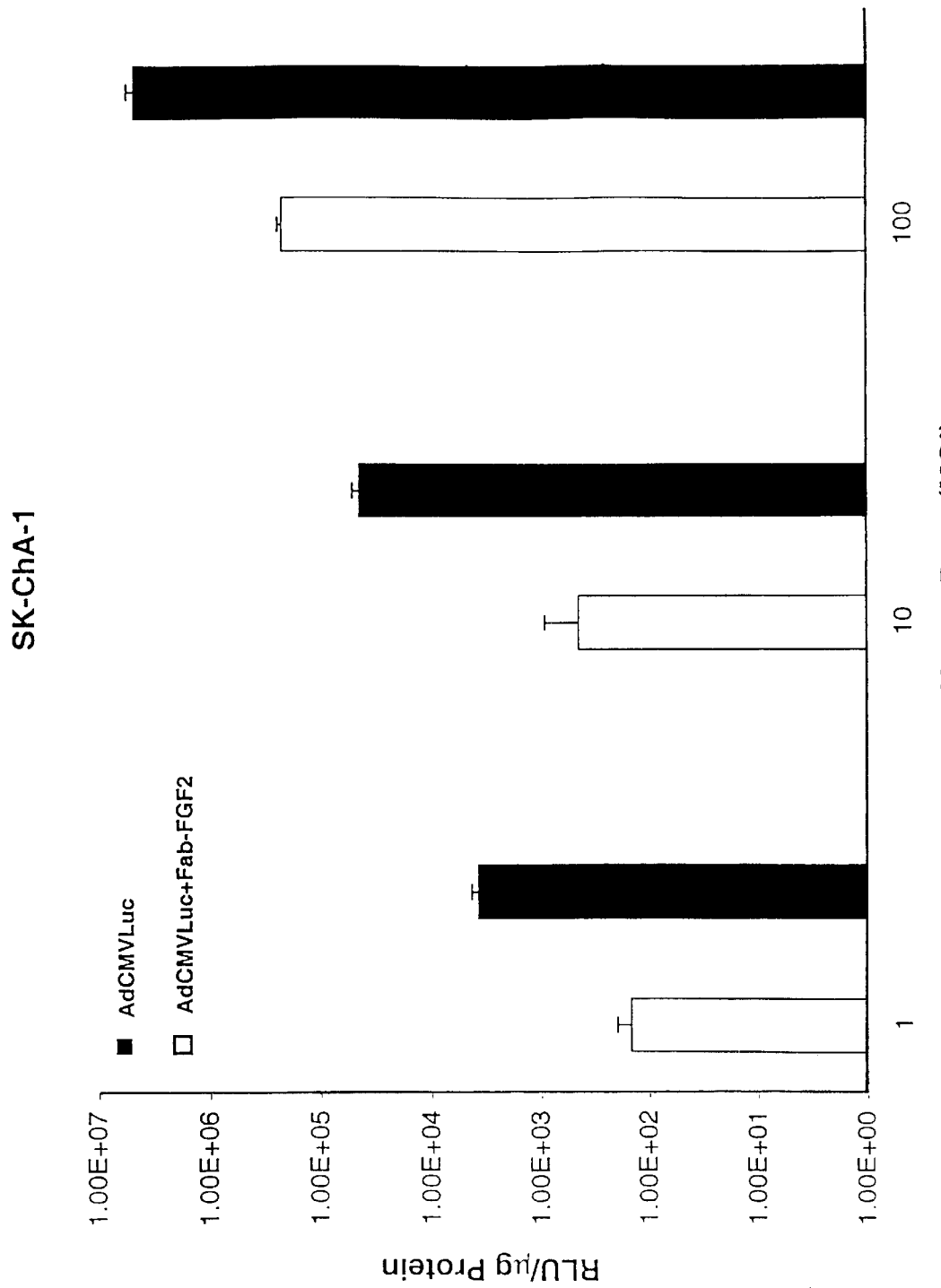

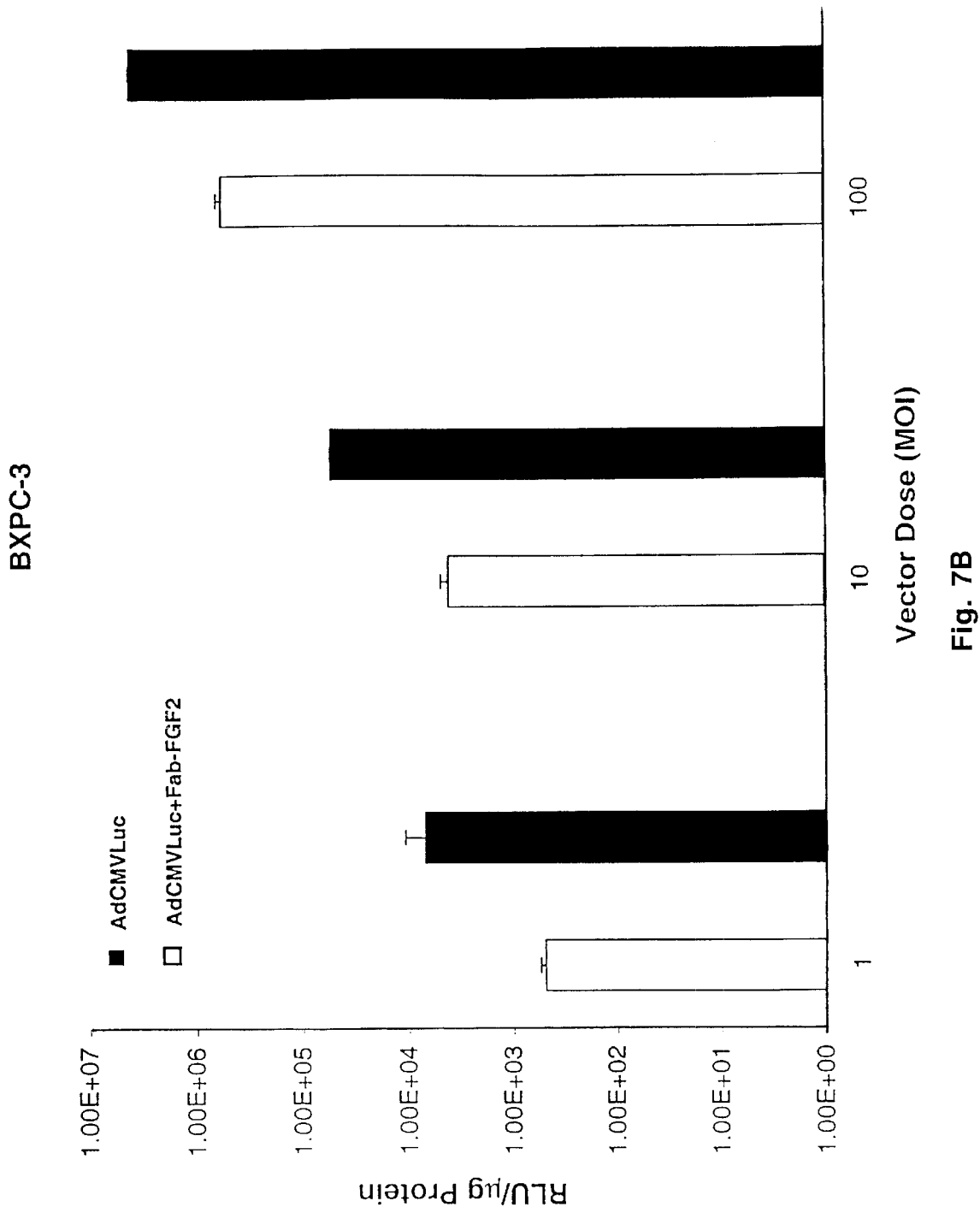

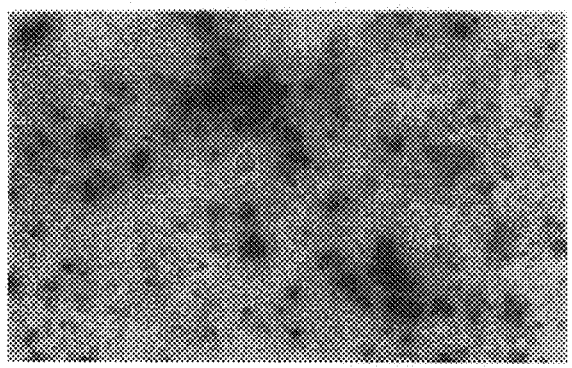 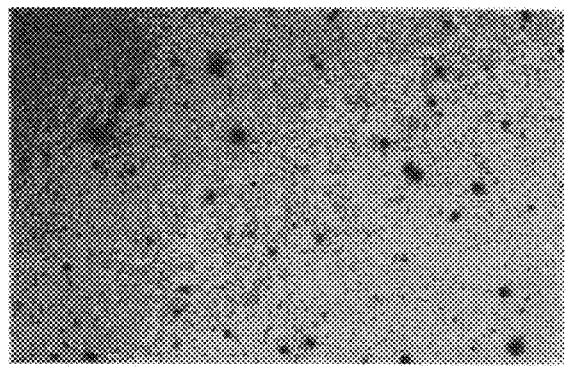
BxPC-3 pancreatic carcinoma SK-ChA-1 cholangiocarcinoma
10 cfu AdCMVLacZ
Fig. 8A 10 cfu AdCMVLacZ +
Fab-FGF2

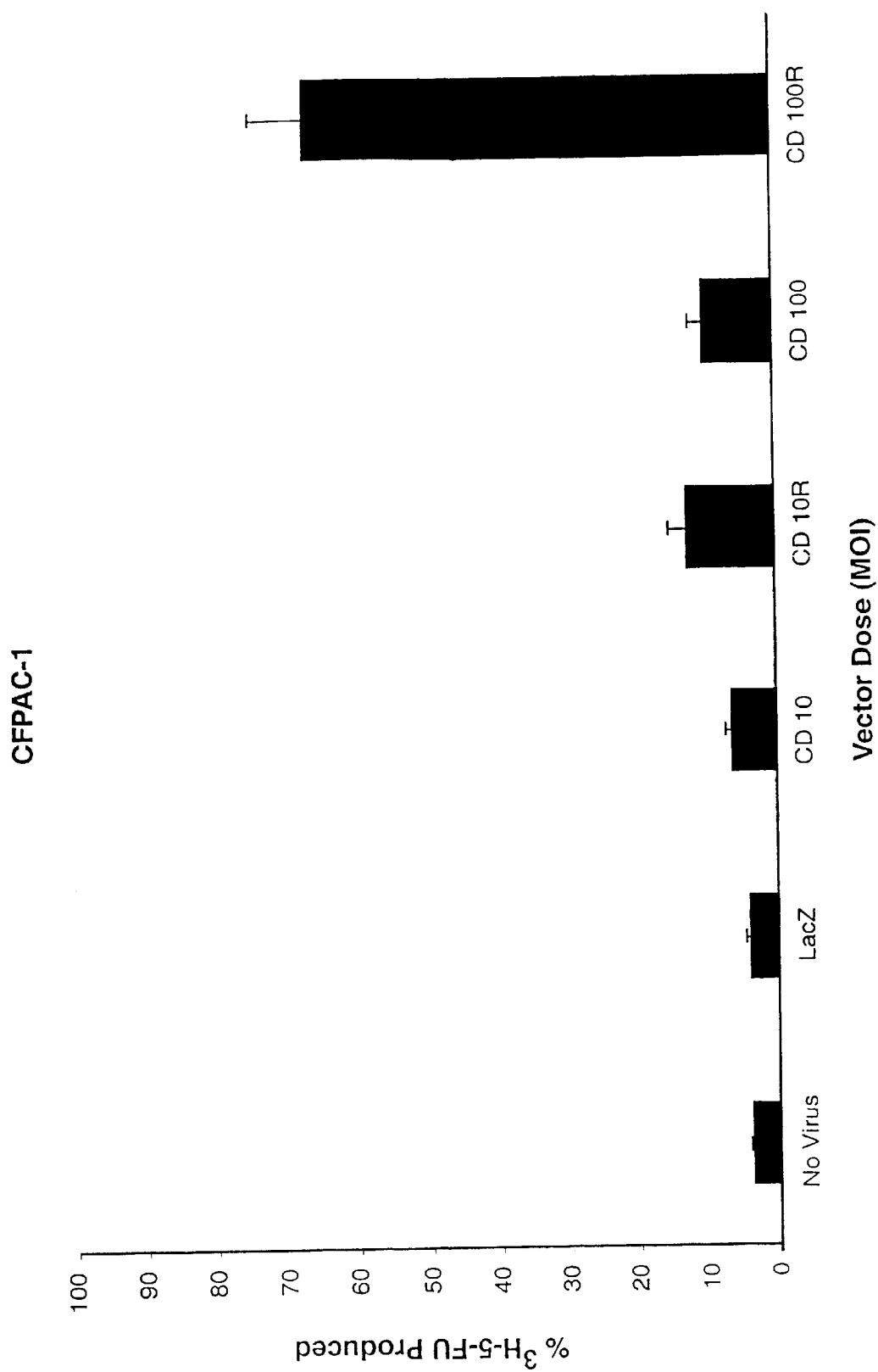

MOLECULAR CHEMOTHERAPY ENHANCEMENT OF RADIOTHERAPY

CROSS-REFERENCE TO RELATED APPLICATION

This patent application claims benefit of provisional patent application U.S. Ser. No. 60/102,391, filed Sep. 29, 1998, now abandoned.

FEDERAL FUNDING LEGEND

This invention was created in part using funds from the federal government. The U.S. government, therefore, has certain rights in this invention.

BACKGROUND OF THE INVENTION

FIELD OF THE INVENTION

The present invention relates generally to the fields of molecular biology, radiation oncology and cancer therapy. More specifically, the present invention relates to the finding that a combination of molecular chemotherapy and radiation therapy enhances therapeutic effects against cancer.

DESCRIPTION OF THE RELATED ART

Clinical applications of cancer gene therapy have had limited success due to a variety of factors, including ineffective therapeutic gene delivery in situ. The physiologic milieu of the target tumor may have deleterious effects on the delivery of therapeutic genes. This limitation may be disease specific, and variable depending on the specific tumor type and tumor location. Most clinical gene therapy trials thus far have utilized compartmental models of malignant disease (1, 2). In this regard, thoracic malignancies and intra-abdominal carcinomatosis represent common body compartmentalized diseases that have been explored in an experimental therapeutic context. Attempts to address the issue of achieving viral vector delivery to cancer cells in the face of a physiologic infection medium of pleural fluid or abdominal ascites have been examined (3, 4). Yang et al. demonstrated retroviral transduction of pancreatic cancer cells in the presence of human ascites, which was similar to the results obtained in culture medium (3). Batra et al. reported significant inhibition of retroviral transduction of mesothelioma cells in the presence of malignant pleural fluid, specifically the chondroitin sulfate proteoglycan fraction (4).

Radiotherapy combined with the radiosensitizing chemotherapeutic drug 5-fluorouracil (5-FU) has been studied as a therapeutic modality in many human tumor types (5). Systemic toxicity limits the amount of 5-FU that can be administered for many clinical anti-cancer applications (6, 7). Radiation therapy and gene therapy have the potential to be combined to enhance effectiveness of cancer therapy without enhancing dose limiting toxicity. To this end, reports have investigated this interaction (8). These include: TNFα under the control of a radiation inducible promoter (9, 10), conversion of prodrugs to toxic metabolites that are also radiosensitizers (11–15), p53 mediated radiosensitization (16, 17) and the genetic induction of membrane receptors that can b e targeted with radiolabeled peptides (18–21).

With respect to enzymatic conversion of nontoxic prodrugs into radiation sensitizing agents, the genes for bacterial and yeast cytosine deaminase (CD) have been cloned and studied (22, 23, 40). Cytosine deaminase converts a nontoxic prodrug 5-fluorocytosine (5-FC) into 5-FU. The cytosine deaminase gene has been used in gene therapy strategies to mediate intracellular conversion of 5-FC to 5-FU, and has been shown to be effective in animal tumor models of human colon carcinoma (24). Human colon cancer cells that have been stably transduced to express the cytosine deaminase gene have been shown to be radiosensitized by the addition of 5-FC in vitro and in vivo (13). Adenoviral vectors have been used to achieve efficient gene delivery in a variety of tissues in vitro and in vivo. Adenoviral vectors encoding the cytosine deaminase gene have been described (25, 26).

Presently available assays for determining intratumoral 5-FU concentration are problematic. They require the removal of a tumor, the homogenization of that tumor and the collection of the cellular lysate in order to directly measure 5-FU concentration, usually by high-pressure liquid chromatography. No noninvasive method of detection existed, which could allow for continuous in vivo monitoring of 5-FU production.

In the context of multiple administrations of adenoviral vectors, the host immunologic response, with generation of neutralizing anti-adenovirus antibodies and cytotoxic T cells, is thought to limit the potential effectiveness of secondary administration of adenoviral vectors. A means to overcome this problem may be to improve the effectiveness of infection of the initial viral challenge, i.e., to enhance the transduction efficiency of the adenoviral vector for the target cells at the initial adenoviral administration. This goal may be achieved by utilizing a ligand to a cellular receptor overexpressed in the target carcinoma cells to redirect adenovirus vector binding.

The prior art is deficient in the lack of effective means of treating of human cancers by chemotherapy combined with radiation therapy to produce enhanced therapeutic effects against cancer and reduced normal tissue toxicity. In addition, the prior art is deficient in the lack of effective means of redirecting adenovirus vector binding via a cellular receptor to improve the effectiveness of gene therapy. Furthermore, the prior art is deficient in the lack of a noninvasive method for continuously monitoring therapeutic transgene expression in tumors therefore improving the gene therapy. The present invention fulfills this long-standing need and desire in the art.

SUMMARY OF THE INVENTION

The present invention is directed to a method of transfecting established tumors in vivo with an adenovirus encoding the cytosine deaminase gene, administration of systemic 5-FC, and radiation therapy, (e.g., external beam or brachytherapy) of the tumor. This method results in tumor regression and prolonged tumor growth inhibition compared to control treatments with molecular chemotherapy or radiation therapy alone. Also disclosed is an adenoviral-conjugate mechanism to circumvent current limitations of cancer gene therapy to solid gastrointestinal malignancies.

Specifically, the present invention utilizes an adenoviral vector under the control of a cytomegalovirus promoter (AdCMVCD) encoding cytosine deaminase in combination with 5-FC and single fraction radiotherapy to demonstrate enhanced cytotoxicity to WiDr human colon carcinoma cells in vitro. The present invention also demonstrates such gene therapy/prodrug treatment strategy employing a fractionated radiation dosing schema in animal models of WiDr human colon carcinoma and SK-ChA-1 human cholangiocarcinoma. A prolonged WiDr tumor regrowth delay was obtained with AdCMVCD infection in combination with systemic delivery of 5-FC and fractionated external beam radiation therapy compared to control animals treated without radiation, without 5-FC, or without AdCMVCD. The present invention further discloses redirection of adenovirus vector (AdCMVCD) binding via a ligand to a cellular receptor, e.g., the basic fibroblast growth factor (FGF2) receptor, to improve the effectiveness of gene therapy in combination with 5-FC treatment and radiation therapy.

Clinical applications for cancer gene therapy are limited by the inability to genetically modify a majority of tumor cells to achieve a therapeutic effect. In this regard, the enzyme/prodrug strategy consisting of cytosine deaminase/5-fluorocytosine (CD/5-FC) relies on diffusion of the cytotoxic enzymatic product 5-FU to kill non-transduced tumor cells. Methods to increase solid tumor transduction in situ may augment therapeutic gene expression and response to therapy. To this end, gene delivery was improved via vector binding to molecules expressed on the cells of tumors. Fibroblast growth factor (FGF) receptors are overexpressed in a majority of pancreatic carcinomas, but poorly characterized in cholangiocarcinoma. Targeted adenovirus via basic fibroblast growth factor (FGF2) to the fibroblast growth factor receptor was used as a vehicle for the delivery of cytosine deaminase to hepatobiliary tumor cells for combination molecular chemotherapy and radiation therapy studies.

FGF2 redirected adenoviral delivery of firefly luciferase gene (AdCMVLuc) expression was evaluated in vitro. Transduction efficiencies using adenoviral delivered *E. coli* β-galactosidase gene (AdCMVLacZ) expression also was determined. The methodology to redirect adenoviral gene delivery employed the Fab fragment of a neutralizing anti-adenoviral knob monoclonal antibody which ablates native adenoviral tropism, conjugated to FGF2 ligand which provides for FGF receptor binding. An adenoviral vector encoding the cytosine deaminase gene (AdCMVCD), in combination with 5-FC and the Fab-FGF2 conjugate, was used to evaluate differential cytosine deaminase protein expression by Western blotting of transfected cell lines and enzymatic activity by increased conversion of $^3$H-5-FC into $^3$H-5-FU. Proliferation assays were performed to correlate differential production of 5-FU with increased cytotoxicity in selected pancreatic and cholangiocarcinoma cell lines. In vivo studies utilizing AdCMVCD, the Fab'-FGF2 conjugate, 5-FC administration, and a single 5 Gy dose of external beam radiation to the tumor in nude mice were performed to evaluate the anti-tumor efficacy of AdCMVCD+Fab'-FGF2, compared to AdCMVCD alone, in established subcutaneous BXPC-3 pancreatic tumors.

In target cells, FGF2 retargeted AdCMVLuc resulted in enhanced (10–100-fold) levels of firefly luciferase expression relative to AdCMVLuc infection alone. X-gal staining for β-galactosidase expression revealed an enhanced transduction frequency mediated by Fab-FGF2 redirected AdCMVLacZ compared to AdCMVLacZ infection alone. Fab-FGF2 redirection of AdCMVCD resulted in increased cellular expression of cytosine deaminase and production of 5-FU, and enhanced cellular cytotoxicity at low viral multiplicities of infection, compared to the levels obtained with AdCMVCD alone. In BXPC-3 tumor-bearing animals treated with AdCMVCD+Fab'-FGF2, 5-FC, and radiotherapy, the time to tumor size doubling was extended compared to AdCMVCD, 5-FC, and radiotherapy alone.

These results indicate that native adenoviral tropism can be redirected using ligands to cell surface receptors. In addition, transduction efficiencies and expression of novel genes introduced via this heterologous pathway are significantly enhanced compared to native adenovirus transduction alone. These findings suggest improved gene expression may be achieved via this adenoviral-conjugate mechanism to circumvent current limitations of cancer gene therapy to solid gastrointestinal malignancies.

The present invention is further directed to a noninvasive method for monitoring the continuous conversion of 5-fluorocytosine to 5-fluorouracil via magnetic resonance spectroscopy (MRS). Magnetic resonance spectroscopy allows for monitoring this prodrug activation therapy through the following: the identification of tumor and normal tissue sites of production or accumulation of 5-fluorouracil, the discrimination of both 5-fluorocytosine clearance/5-fluorouracil production, the determination of the residence time of 5-fluorouracil, the production of metabolites of the active drug, along with the determination of the elimination kinetics of 5-fluorouracil from tumor and normal organs. The information that magnetic resonance spectroscopy can provide about the pharmacokinetics of these agents can help develop procedures to maximize the effectiveness of this therapy with the potential to maximize tumor regression.

In one embodiment of the present invention, there is provided a method of treating an individual having a solid tumor, comprising the steps of treating the individual with an adenovirus encoding a cytosine deaminase gene; administering 5-fluorocytosine to the individual; and treating the individual with radiation therapy.

In another embodiment of the present invention, there is provided a method of treating an individual having a cancer, comprising the steps of combining a ligand that binds to a tumor cellular receptor and an adenoviral vector encoding a cytosine deaminase gene to form a complex; treating the individual with the complex; administering 5-fluorocytosine to the individual; and treating the individual with external beam irradiation.

In still another embodiment of the present invention, there is provided a method of monitoring continuous conversion of 5-fluorocytosine to 5-fluorouracil in a tumor, wherein the tumor is treated with multiple doses of 5-fluorocytosine and multiple doses of adenovirus encoding a cytosine deaminase gene, comprising the steps of placing the treated tumor in a magnet; and evaluating the presence of 5-fluorocytosine and 5-fluorouracil by magnetic resonance spectroscopy over a course of time, wherein less amount of 5-fluorocytosine and more amount of 5-fluorouracil indicates increased conversion of 5-fluorocytosine to 5-fluorouracil. Preferably, the tumor is further treated with radiation.

In still yet another embodiment of the present invention, there is provided a method of monitoring continuous conversion of 5-fluorocytosine to 5-fluorouracil in a tumor, wherein the tumor is treated with multiple doses of 5-fluorocytosine and multiple doses of cytosine deaminase gene encoding adenovirus targeted by a ligand to a tumor cellular receptor, comprising the steps of placing the treated tumor in a magnet; and evaluating the presence of 5-fluorocytosine and 5-fluorouracil by magnetic resonance spectroscopy over a course of time, wherein less amount of 5-fluorocytosine and more amount of 5-fluorouracil indicates increased conversion of 5-fluorocytosine to 5-fluorouracil. Preferably, the tumor is further treated with radiation.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 7A–7B show differential luciferase expression in pancreatic and cholangiocarcinoma cells infected with AdCMVLuc or FGF2-redirected AdCMVLuc adenoviral vector. SK-ChA-1 cholangiocarcinoma cells (FIG. 7A) and BXPC-3 cells (FIG. 7B) were infected with AdCMVLuc or AdCMVLuc+Fab-FGF2 to determine whether differential luciferase expression results from redirection with the Fab-FGF2 conjugate. Cells were infected with 1, 10 or 100 MOI at 37° C. for 2 hours, then complete media added to the plate. Twenty-four hours later, cell lysates were evaluated for luciferase activity. Fab-FGF2-retargeted AdCMVLuc resulted in increased levels of luciferase expression relative to AdCMVLuc alone.

FIG. 8 shows that Fab-FGF2-retargeted AdCMVLacZ resulted in enhanced transduction efficiency of pancreatic and cholangiocarcinoma cells. BXPC-3 pancreatic carcinoma cells and SK-ChA-1 cholangiocarcinoma cells were infected with AdCMVLacZ or AdCMVLacZ+Fab-FGF2 at a MOI of 10. Forty-eight hours later, X-gal staining was performed. FIG. 8A shows BXPC-3 and SK-ChA-1 cells infected with AdCMVLacZ alone.

FIG. 9 shows retargeted transfection (R) with AdCMVCD+Fab-FGF2 in five cell lines was evaluated, by Western, with each cell line on a separate gel. On each gel, six lanes were run at the MOI listed. Cells were transduced with either AdCMVCD or AdCMVCD-Fab-FGF2 or mock transfection. Cell extracts were prepared and equal protein loaded per well.

FIGS. 10A–10C show CD mediated conversion of 5-FC to 5-FU in pancreatic and cholangiocarcinoma cells. SK-ChA-1 (FIG. 10A), BXPC-3 (FIG. 10B) or CFPAC-1 (FIG. 10C) cells were infected with AdCMVCD or AdCMVCD+Fab-FGF2 at various MOI. Cells were harvested and lysed and 6–10 μg protein was incubated with

[6-$^3$H]-5-FC at 37° C. for 6 hours. Each reaction mixture plus 5-FU and 5-FC standards were then spotted on a cellulose thin layer chromatography plate. Each region (5-FU and 5-FC) was counted for radioactivity. Percent conversion of 5-FC to 5-FU was calculated as activity in the 5-FU fraction compared to the total counts in the 5-FC and 5-FU fractions. Controls included uninfected cells and AdCMVLacZ infected cells.

Figure 11A:
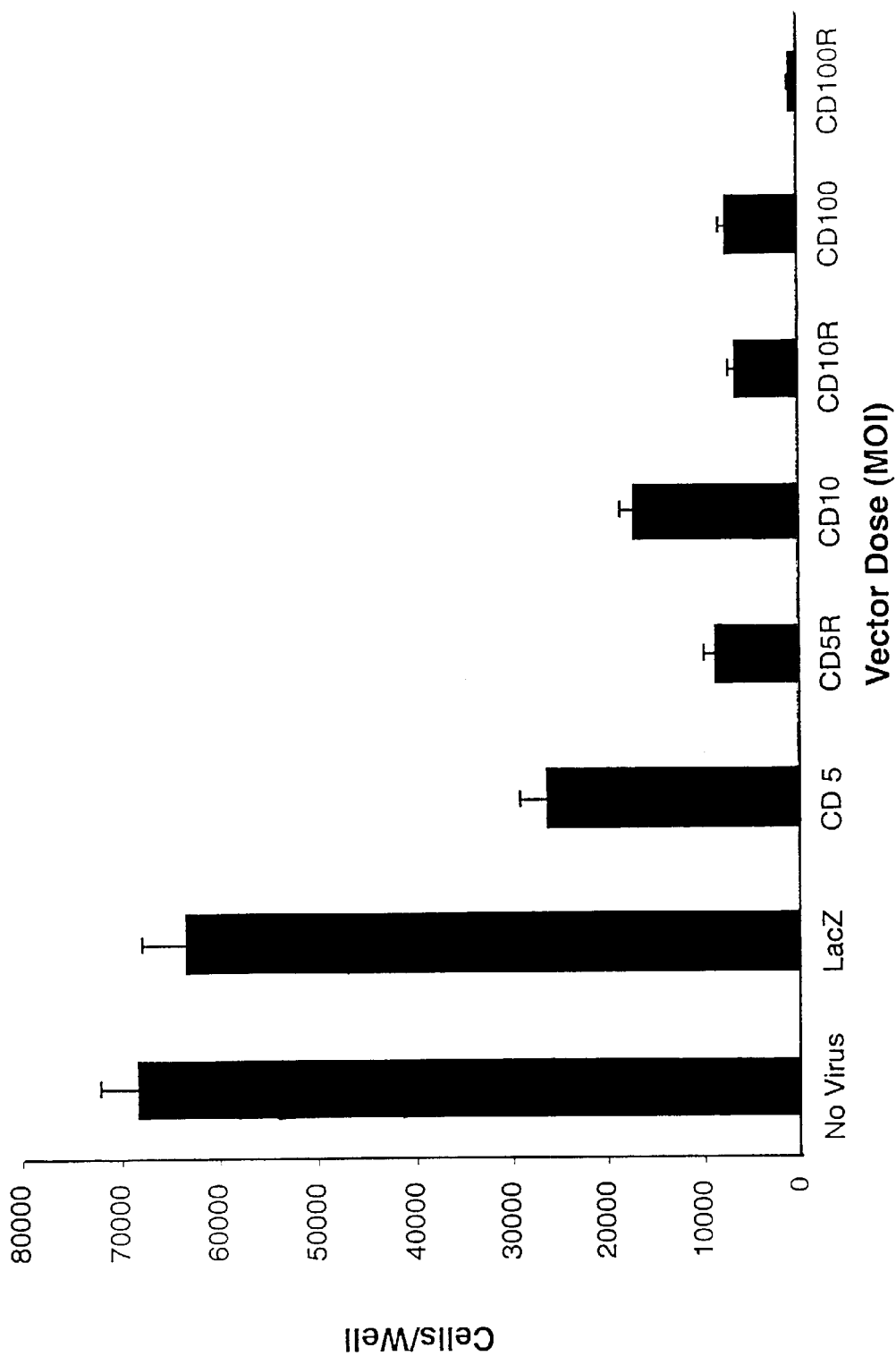
Figure 11B:
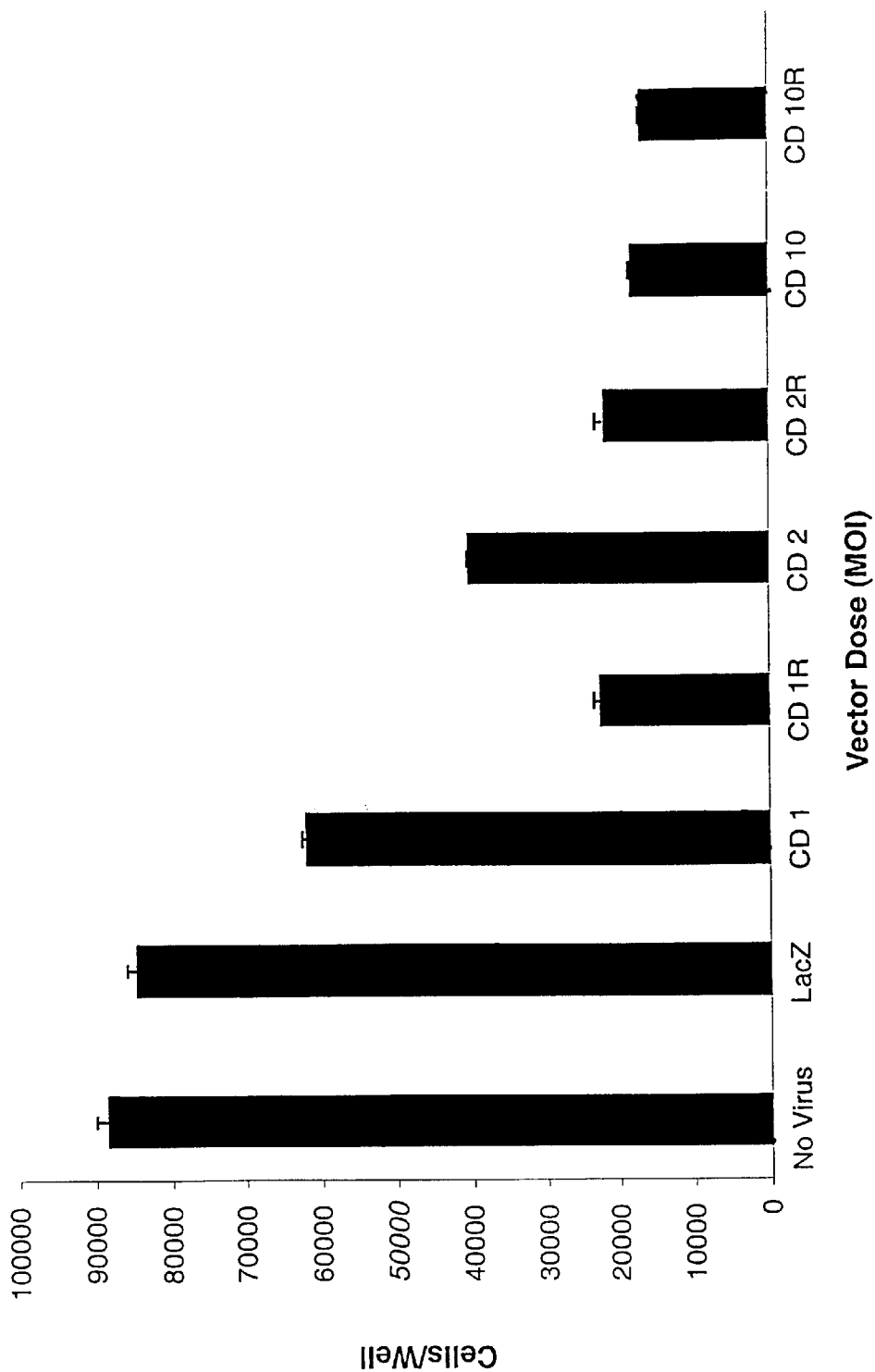
Figure 11C:
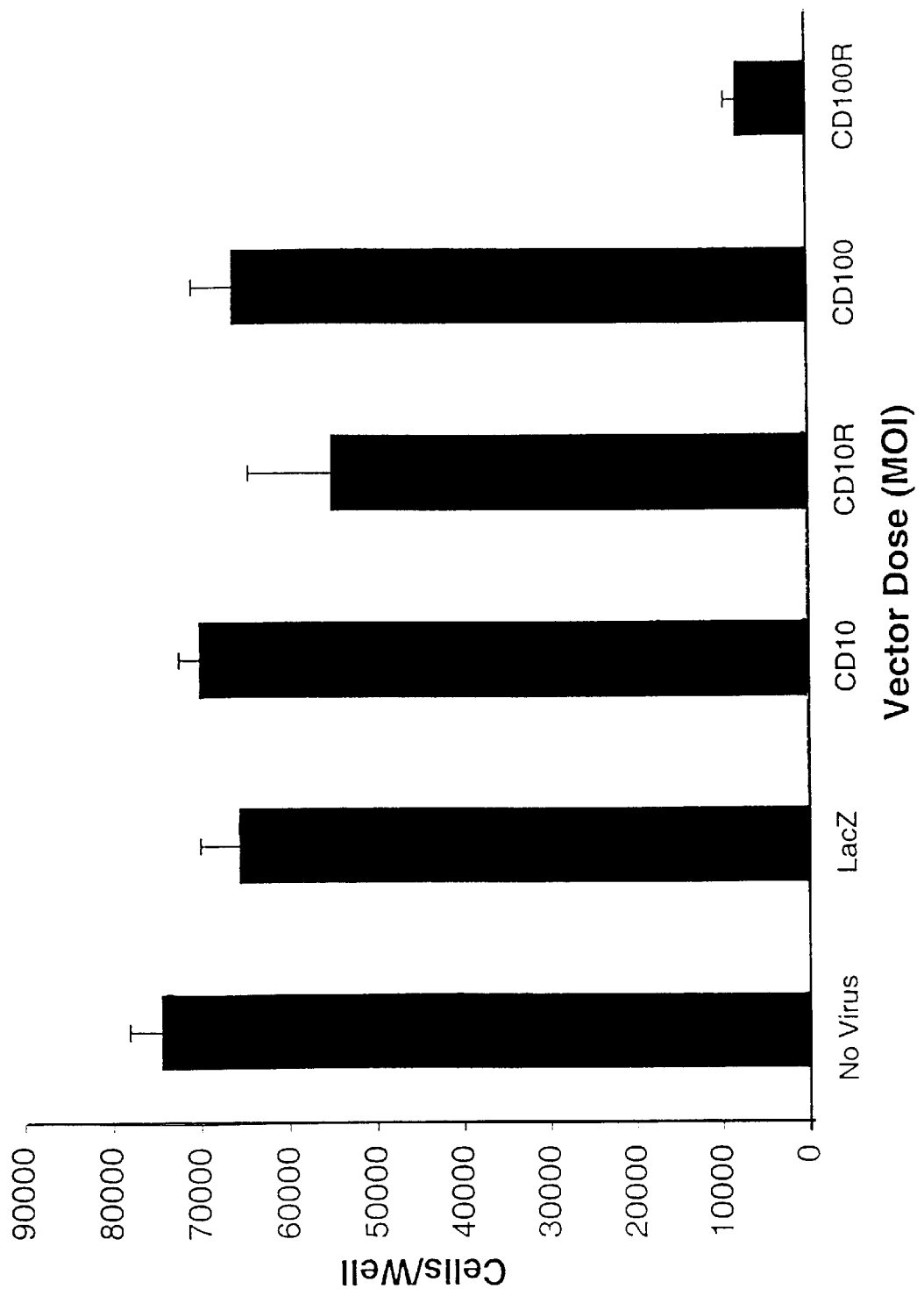

FIGS. 11A–11C show CD mediated cytotoxicity to pancreatic and cholangiocarcinoma cells following infection with AdCMVCD or AdCMVCD+Fab-FGF2. SK-ChA-1 (FIG. 11A), BXPC-3 (FIG. 11B) or CFPAC-1 (FIG. 11C) cells were infected at a confluency of 80% with AdCMVCD or AdCMVCD+Fab-FGF2. Controls included AdCMVLacZ or no virus. Twenty-four hours later, cells were trypsinized, counted and plated in 96-well plates with media containing 5 μg/ml 5-FC. Cell proliferation was determined b y tetrazolium salt (MTS) colorimetric assay after 6–8 days of incubation.

Figure 12:
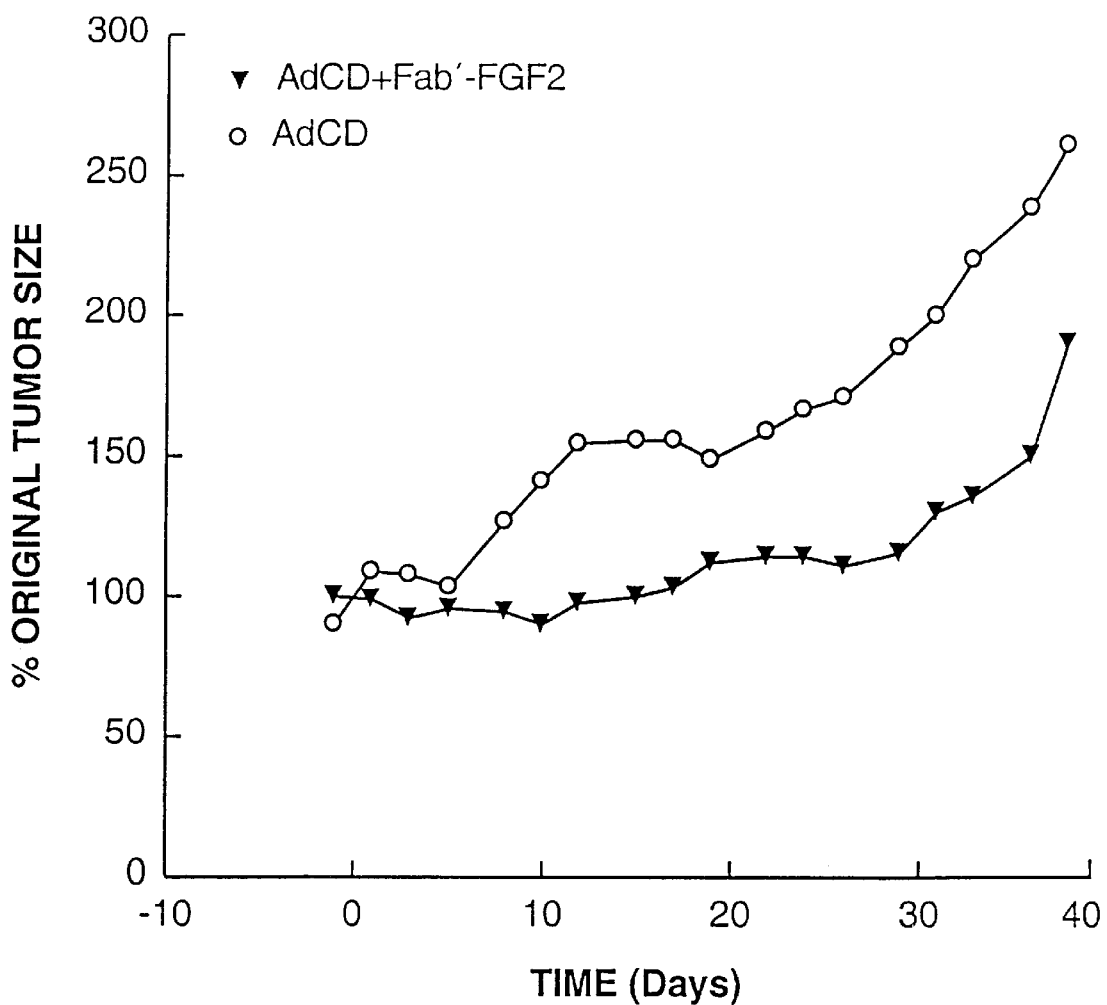

FIG. 12 shows growth of BXPC-3 tumors following treatment with AdCMVCD or AdCMVCD+Fab'-FGF2, 5-FC, and 5 Gy radiation. Mice received 2×10 BXPC-3 cells by s.c. injection, and tumors with diameters of 5 to 10 mm formed in 7 days. At this time, AdCMVCD or AdCMVCD+Fab'-FGF2 ($5\times10^7$ pfu) was administered by intratumoral injection on Day −2 relative to radiation treatment. All animals received 5-FC (400 mg/kg twice daily by i.p. injection) beginning on Day −2 for 7 days. Animals received 5 Gy $^{60}$Co (Day 0) to their tumor. Data points represent the mean change in tumor surface area relative to Day 0. n=5 tumors/group.

Figure 13:
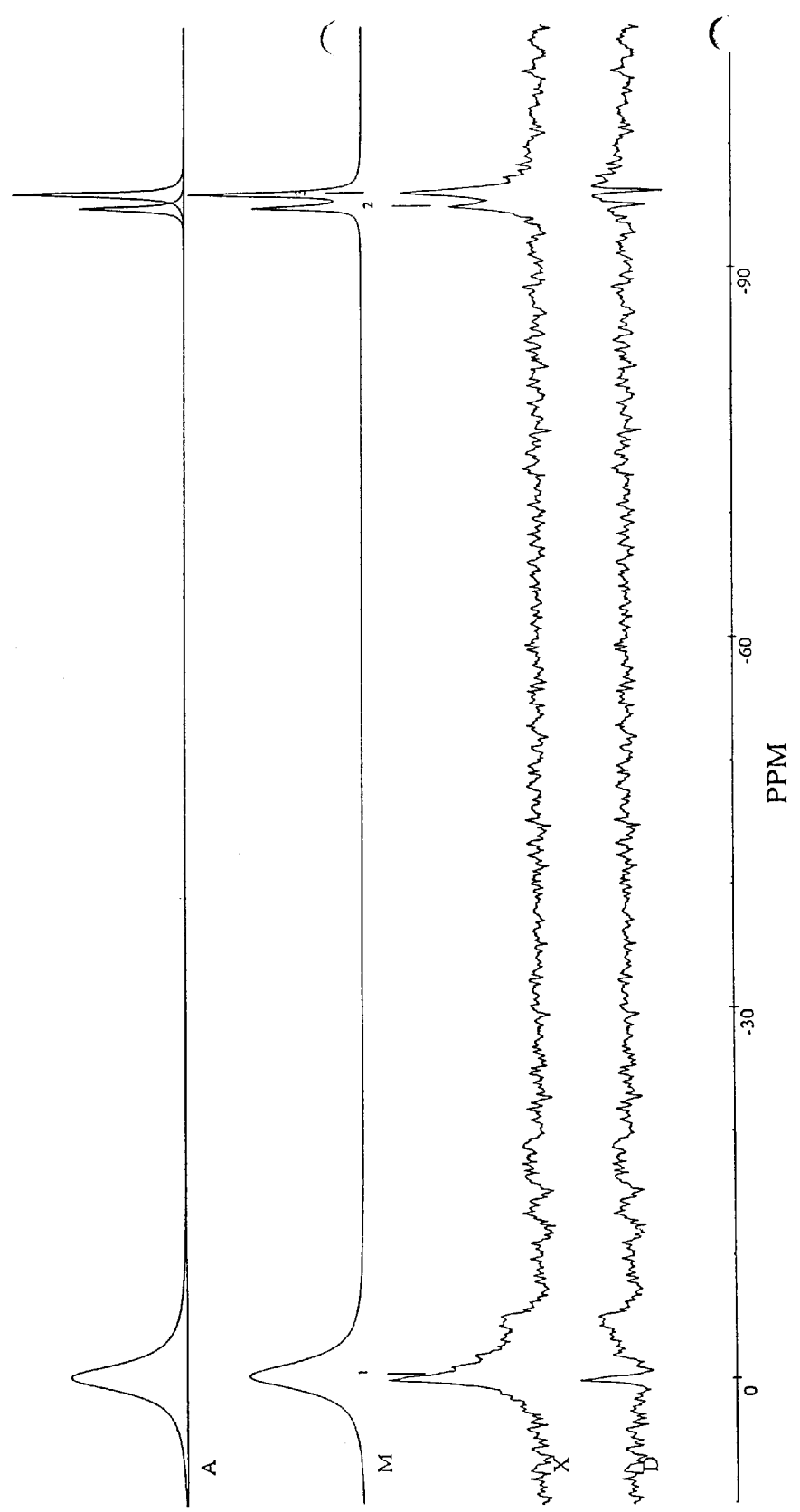

FIG. 13 shows a significant peak for 5-FU at the initial time point when evaluated by MRS. $2\times10^7$ LS174T cells transfected at a MOI of 100 with AdCMVCD were injected into a subcutaneous area in the flank of a nude mouse. Locally, approximately 50 microliters of 3.8 mM 5-FC were injected at the site of the tumor after which these animals were placed in the magnet and evaluated for the presence of 5-FC and the conversion of 5-FC to 5-FU by the adenoviral cytosine deaminase gene.

Figure 14:
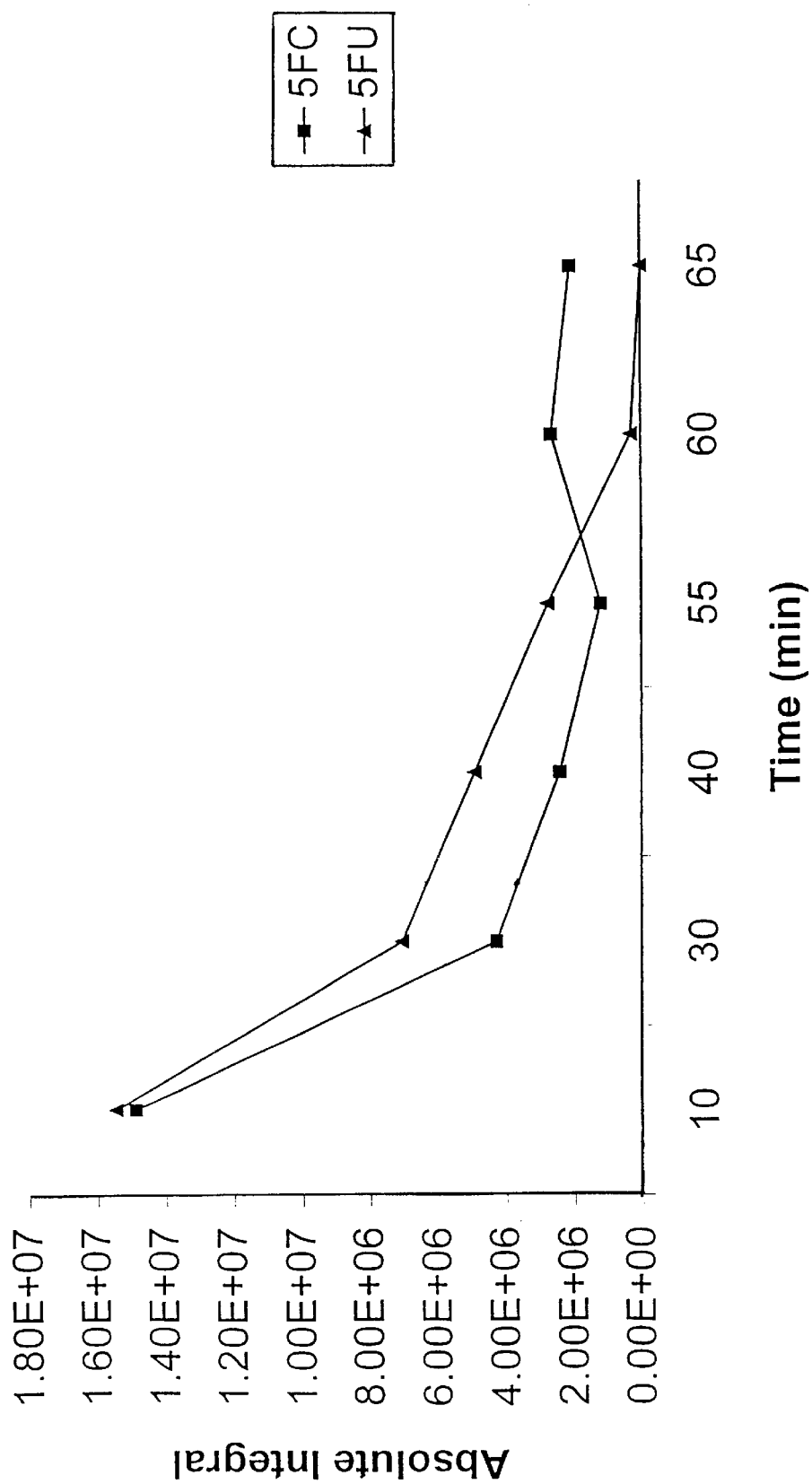

FIG. 14 shows that the integral of the 5-FU peak exceeded that of the 5-FC peak for 55 minutes. The experimental procedure is the same as that in FIG. 13.

DETAILED DESCRIPTION OF THE INVENTION

The present invention concerns in vivo transfection of cancer cells in solid tumors with an adenovirus encoding the cytosine deaminase gene, administration of systemic 5-FC, and radiation therapy of the tumor which resulted in tumor regression and prolonged tumor growth inhibition compared to control treatments with molecular chemotherapy or radiation therapy alone. This is the first description of how to transfect established tumors in vivo with the cytosine deaminase gene to produce enhanced therapeutic effects with the combination of molecular chemotherapy and radiation therapy. Conventional systemic administration of 5-FU produces dose limiting normal tissue toxicity. The local production of 5-FU within a tumor transfected with the cytosine deaminase gene and systemic administration of 5-FC, results in higher intratumor concentrations of 5-FU than achievable with systemic administration of 5-FU, thus improving the therapeutic ratio in combination with radiotherapy. The combination of molecular chemotherapy and radiation therapy improves treatment of a variety of cancers in humans including colon cancer, pancreatic cancer, prostate cancer, lung cancer, brain cancer, head and neck cancer and cholangiocarcinoma.

The present invention can be utilized in local and regional situations where the cancer is accessible for intratumor or regional injection of the cytosine deaminase vector. Tropism-modified adenovirus or an adenovirus encoding the cytosine deaminase gene under control of a tumor specific promoter may be required for selective gene delivery to disseminated metastatic cancer. Native adenoviral tropism can be redirected through other cell surface receptors, such as fibroblast growth factor (FGF) receptor. The present invention used targeted adenovirus to the FGF receptor as a vehicle for the delivery of cytosine deaminase to hepatobiliary tumor cells for combination of molecular chemotherapy and radiation therapy studies. The results suggest that improved gene expression may be achieved via this adenoviral-conjugate mechanism to circumvent current limitations of cancer gene therapy to solid gastrointestinal malignancies.

Thus, the present invention provides a method of treating an individual having a solid tumor, comprising the steps of treating the individual with an adenovirus encoding a cytosine deaminase gene; administering 5-FC to the individual; and treating the individual with external beam irradiation. Representative cancers treated using this method include colon cancer, pancreatic cancer, prostate cancer, lung cancer, brain cancer, head and neck cancer or cholangiocarcinoma. Preferably, the adenovirus is under control of a promoter or tumor specific promoter such as a carcinoembryonic antigen promoter, DF3/MUC1 promoter, a prostate specific antigen promoter, surfactant protein A promoter, leukoprotease inhibitor promoter, erbB-2 promoter, alpha fetoprotein promoter and E2F promoter.

Generally, any adenovirus encoding a cytosine deaminase gene may be used in the methods taught herein; one example is the *E. coli* cytosine deaminase gene. In this method, 5-FC is typically administered in a dosage of about 400–500 mg/kg twice daily and the external beam radiation is generally applied daily at a single dose of from about 2 Gy to about 3 Gy over a 4 to 6 week period. Alternatively, brachytherapy can be used as the radiation therapy. This produces greater cytotoxicity of neoplastic cells compared to treatment with adenovirus alone or external beam radiation alone.

The present invention is also directed to a method of treating an individual having a cancer, comprising the steps of combining a ligand that binds to a tumor cellular receptor and an adenoviral vector encoding a cytosine deaminase gene to form a complex; treating the individual with the complex; administering 5-FC to the individual; and treating the individual with radiation therapy. Preferably, the tumor receptor binds to the adenoviral vector. Representative cancers treated using this method include colon cancer, pancreatic cancer, prostate cancer, lung cancer, brain cancer and cholangiocarcinoma. Generally, the ligand to cellular receptor is selected from the group consisting of basic fibroblast growth factor (FGF2), epidermal growth factor and antibodies to growth factor receptors.

Preferably, the adenovirus is under control of a promoter. Generally, any adenovirus encoding a cytosine deaminase gene may be used in the methods taught herein; one example is the *E. coli* cytosine deaminase gene. In this method, 5-FC is typically administered in a dosage of from about 400–500 mg/kg twice daily and the external beam radiation is generally applied daily at a single dose of from about 2 Gy to about 3 Gy over a 4 to 6 week period. Alternatively, brachytherapy can be used as the radiation therapy. This produces greater cytotoxicity of neoplastic cells compared to treatment with adenovirus alone or external beam radiation alone.

The present invention further discloses a noninvasive method for continuous in vivo monitoring of 5-FU production via magnetic resonance spectroscopy (MRS). Magnetic resonance spectroscopy is capable of monitoring the biodistribution of 5-FU secondary to its ability to detect fluorine-19. Magnetic resonance spectroscopy has been able to discriminate between both the prodrug (5-FC), the active drug (5-FU) and some of the active fluorinated metabolites. The benefits of using magnetic resonance spectroscopy for detecting fluorinated compounds include the following: high detection sensitivity, low background signal, 100% natural abundance and a spin of ½ (41).

The present invention uses magnetic resonance spectroscopy to monitor 5-FU concentrations in vivo following intratumoral injection of an adenovirus encoding the gene for cytosine deaminase and intravenous injection of 5-FC b.i.d for 5 days. Subcutaneous and metastatic pancreatic and colon cancer models will be used to monitor the pharmacokinetics of 5-FU production and elimination from tumor and normal organs after transfecting these tumors with cytosine deaminase containing adenovirus.

There is a need for continuous production of 5-FU at the site of a tumor mass to maximize therapeutic efficacy and a means to detect and quantitate its concentration in tumor and in normal tissues over time in order to develop procedures that maximize 5-FU production. Magnetic resonance spectroscopy allows for monitoring this prodrug activation therapy through the following: the identification of tumor and normal tissue sites of production or accumulation of 5-FU, the discrimination of both 5-FC clearance/5-FU production, the determination of the residence time of 5-FU, the production of metabolites of the active drug, along with the determination of the elimination kinetics of 5-FU from tumor and normal organs. The information that magnetic resonance spectroscopy can provide about the pharmacokinetics of these agents can help develop procedures to maximize the effectiveness of this therapy with the potential to maximize tumor regression.

Previous studies using magnetic resonance spectroscopy did not take into account the effects of multiple dosing of the prodrug 5-FC in order to help maintain a continuous production of 5-FU or the use of multiple injections of an adenoviral vector to maximize cytosine deaminase gene transfer (41). Given the desire to maintain a continuous production of 5-FU, it is proposed that magnetic resonance spectroscopy could aid in guiding the dosing of the prodrug and the adenovirus along with monitoring the formation/elimination of 5-FU. Thus, the information that magnetic resonance spectroscopy can provide concerning the pharmacokinetics of 5-FU would be valuable for further development of prodrug activation gene therapy approach and provide the utility for further application to human clinical trials.

In still another embodiment of the present invention, there is provided a method of monitoring continuous conversion of 5-fluorocytosine to 5-fluorouracil in a tumor, wherein the tumor is treated with multiple doses of 5-fluorocytosine and multiple doses of adenovirus encoding a cytosine deaminase gene, comprising the steps of placing the treated tumor in a magnet; and evaluating the presence of 5-fluorocytosine and 5-fluorouracil by magnetic resonance spectroscopy over a course of time, wherein less amount of 5-fluorocytosine and more amount of 5-fluorouracil indicates increased conversion of 5-fluorocytosine to 5-fluorouracil. Preferably, the tumor is further treated with radiation.

In still yet another embodiment of the present invention, there is provided a method of monitoring continuous conversion of 5-fluorocytosine to 5-fluorouracil in a tumor, wherein the tumor is treated with multiple doses of 5-fluorocytosine and multiple doses of cytosine deaminase gene encoding adenovirus targeted by a ligand to a tumor cellular receptor, comprising the steps of placing the treated tumor in a magnet; and evaluating the presence of 5-fluorocytosine and 5-fluorouracil by magnetic resonance spectroscopy over a course of time, wherein less amount of 5-fluorocytosine and more amount of 5-fluorouracil indicates increased conversion of 5-fluorocytosine to 5-fluorouracil. Preferably, the tumor is further treated with radiation.

The following examples are given for the purpose of illustrating various embodiments of the invention and are not meant to limit the present invention in any fashion.

EXAMPLE 1

Cell Culture

The human colon carcinoma cell line WiDr (ATCC CCL-218 Rockville, Md.) was grown in Earle's modified Eagle's medium (EMEM) (Gibco-BRL, Grand Island, N.Y.) supplemented with 10% fetal bovine serum (FBS) (Summit, Fort Collins, Colo.), 2 mM glutamine, and 1% non-essential amino acids in a humidified atmosphere with 5% $CO_2$. The human cholangiocarcinoma cell line SK-ChA-1 was the gift of A. Knuth, Ludwig Institute for Cancer Research, London, UK. SK-ChA-1 cells were maintained in RPMI-1640 medium supplemented with 2 mM L-glutamine and 10% FBS at 37° C. in a humidified 5% $CO_2$ atmosphere. The transformed human embryonal kidney cell line, 293, is an E1A transcomplementing cell line (Microbix, Toronto, Canada) utilized for viral propagation and titering and was maintained in Dulbecco's Modified Eagle's medium-F12 supplemented with 2 mM L-glutamine and 10% FBS at 37° C. in a humidified 5% $CO_2$ atmosphere. The cells were passaged using 0.05% trypsin and 5 mM EDTA once weekly.

EXAMPLE 2

Chemotherapeutic Drugs

5-FC (Sigma, St. Louis, Mo.) was dissolved in PBS at a stock concentration of 10 mg/ml. 5-FU (50 mg/ml, Hoffman-LaRoche, Inc., Nutley, N.J.) was used as a control for standard clinical therapy of both colon and cholangiocarcinoma in current medical practice.

EXAMPLE 3

Adenovirus Production and Characterization

The production, characterization, and functional validation of the AdCMVCD vector was described (14, 15). Briefly, the cytosine deaminase gene was cloned into the adenoviral shuttle vector pACCMVpLpARS (+) (provided by R. Gerard, Katholieke Universiteit Leuven, Ontario, Canada) and then co-transfected with the pJM17 rescue plasmid (provided by Dr. F. Graham, McMaster University) into 293 cells to allow for homologous recombination (28). Individual plaques were isolated and subjected to 2 further rounds of plaque purification. The final adenovirus was validated by PCR and restriction analysis. The ability of AdCMVCD to induce a functional cytosine deaminase enzyme was determined using a n assay to measure conversion of $^3$H-5-FC to $^3$H-5-FU by infected cell lysate (26).

EXAMPLE 4

In Vitro Radiation Dose Response Analysis

WiDr human colon cancer cells were plated at a density of $5 \times 10^5$ cells/well in 6-well tissue culture plates 24 hours prior to adenoviral infection. WiDr cells were then infected with AdCMVCD at a multiplicity of infection (MOI) of 1 or 10 plaque forming units (pfu) per cell in 0.5 ml Opti-Mem (Gibco-BRL) for 1.5 hours. A control virus that encodes the reporter gene E. coli LacZ which produces β-galactosidase (AdCMVLacZ) was provided by Dr. De-Chu Tang, University of Alabama at Birmingham. Viral infection was stopped by the addition of 3 ml of complete growth media and the cells were returned to the incubator overnight. The following day, media was replaced with media supplemented with the appropriate concentration of 5-FC or no drug. The cells were then incubated in 5-FC for 3 days. The cells were then mock irradiated or irradiated on ice using a Picker $^{60}$Co therapy unit (Cleveland, Ohio) at a dose rate of 80 cGy/min. The cells were then plated for colony formation. Colonies formed in 14 days and were fixed in ethanol and stained with 1% crystal violet.

SK-ChA-1 cells were infected with 10 MOI of AdCMVCD, or AdCMVLacZ, treated with 0, 10 or 20 μg/ml 5-FC for 72 hours, then irradiated with 0 or 8 Gy (80 cGy/min). The cells were irradiated on ice, then trypsinized, counted and plated in triplicate in 25 cm$^2$ tissue culture dishes (Costar) in media free of 5-FC. The plates were fixed and stained 14 days later. For both WiDr and SK-ChA-1 cells, colonies containing greater than 50 cells were counted. Percent survival was calculated as the average number of colonies counted divided by the number of cells plated times plating efficiency (PE); where PE was the fraction of colonies counted divided by cells plated without radiation. The dose response curve was fitted using the Fit v 2.4 software (provided by Dr. N. Albright, University of California at San Francisco, San Francisco, Calif.).

EXAMPLE 5

Animal Studies

Athymic nude mice (Frederick Cancer Research Laboratory, Bethesda, Md.) were injected s.c. in the flank with 2×10 WiDr or SK-ChA-1 cells. Tumors were allowed to grow for 7 days at which time they were divided into various treatment groups. The WiDr tumor treatment groups included: 1) AdCMVCD, 5-FC and a single 10 Gy dose of $^{60}$Co radiation; 2) AdCMVCD, 5-FC and 3×5 Gy fractions of $^{60}$Co radiation; 3) No virus, 5-FC and 3×5 Gy fractions of $^{60}$Co radiation; 4) AdCMVCD, 5-FC and no radiation. The AdCMVCD vector was injected intratumorally (i.t.) once every other day for a total of 3 injections beginning at Day −2 relative to radiation. The 5-FC was administered for 7 days as 500 mg/kg twice daily by i.p. injection beginning at Day −2 relative to radiation. Two days following the initial adenoviral and 5-FC injection, mice were anesthetized with ketamine-HCI (Phoenix Scientific, Inc., St. Joseph, Mo.) and irradiated. The first 5 Gy fraction was given followed by 2 subsequent 5 Gy fractions given daily. The 10 Gy single dose was given on the same day as the second 5 Gy fraction.

The SK-ChA-1 tumor treatment groups included: 1) AdCMVCD, 5-FC, and 5×2 Gy, 2) AdCMVCD, 5-FC, without radiation, 3) 5-FU (30 mg/kg/day as 15 mg/kg twice daily) without radiation, 4) 5×2 Gy radiation and 5-FU (30 mg/kg/day as 15 mg/kg twice daily), and 5) no treatment. The mice with SK-ChA-1 tumors received 5-FC (400 mg/kg twice daily by i.p. injection) beginning a t Day −2 relative to radiation therapy, and continued for 7 days. The mice were anesthetized with ketamine-HCl, and their tumors irradiated using the Picker $^{60}$Co therapy unit. All mice were shielded with a specially designed lead apparatus that allowed irradiation of a single flank (6 mice at a time). Tumor growth was measured 3 times weekly in 2 dimensions using a Vernier caliper and the tumor size (length× width) was calculated. The animals were maintained in a laminar flow room and fed sterilized chow and tap water in accordance with University of Alabama Animal Resource Department protocols.

EXAMPLE 6

Statistical Methods

The logrank test was used to assess if there were differences among the four groups of animals bearing WiDr xenografts in overall survival, time to tumor doubling, and time to regrowth. Specific pairwise comparisons between treatment groups for time to tumor regrowth and time to tumor doubling were also made using the logrank test. Fisher's Exact test was used to assess if there were any differences in tumor regression rate between groups.

The logrank test was used to assess if there were differences among the five groups of animals bearing SK-ChA-1 xenografts in time to tumor doubling and time to regrowth. Specific pairwise comparisons were made between treatment groups for time to tumor regrowth due to lack of an overall difference in time to tumor doubling. The level of significance used for all comparisons was P<0.05.

EXAMPLE 7

Results

Figure 1:
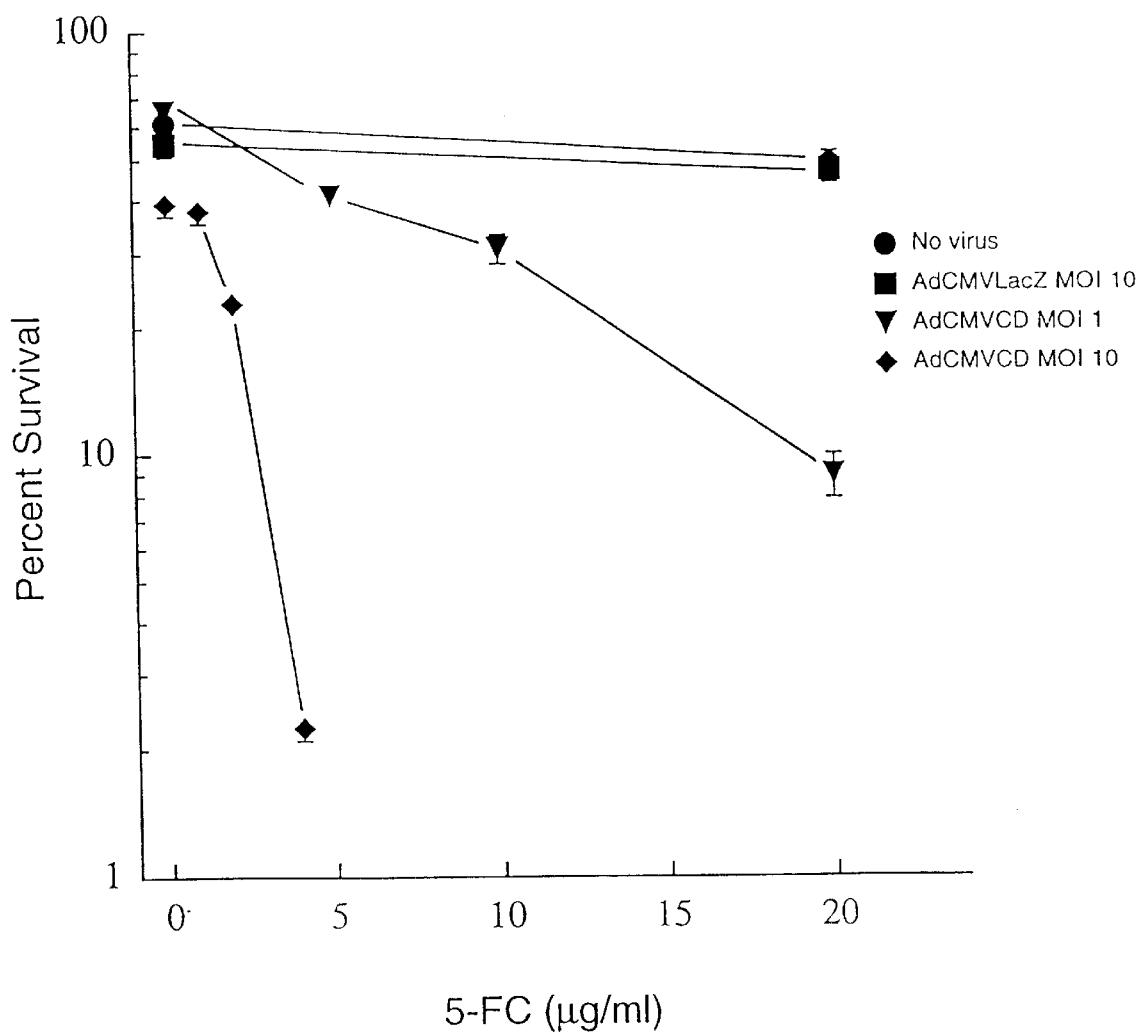
FIG. 1 shows survival of WiDr cells infected with AdCMVCD at MOIs of 1 and 10 and exposed to 5-FC for 3 days prior to plating for colony formation. Uninfected and AdCMVLacZ infected WiDr cells with and without 5-FC served as controls. The values represent the mean of 2–6 experiments done in triplicate determinations for each condition. Error bars represent the standard error of the mean.

The ability of AdCMVCD infection combined with 5-FC to kill WiDr cells was tested. Survival was determined following AdCMVCD infection at MOI's of 1 and 10 with varying concentrations of 5-FC (FIG. 1). Increased cytotoxicity at each MOI of AdCMVCD infection with increasing 5-FC concentration was observed in the WiDr cells. Maximal cell killing was observed at 1 and 10 MOI with administration of 20 and 4 μg/ml 5-FC, respectively. No changes in cytotoxicity were observed for the AdCMVLacZ or no virus control at the maximum tested 5-FC concentration (20 μg/ml). The survival level obtained with virus and prodrug was used to normalize for the combination radiation survival values.

Figure 2:
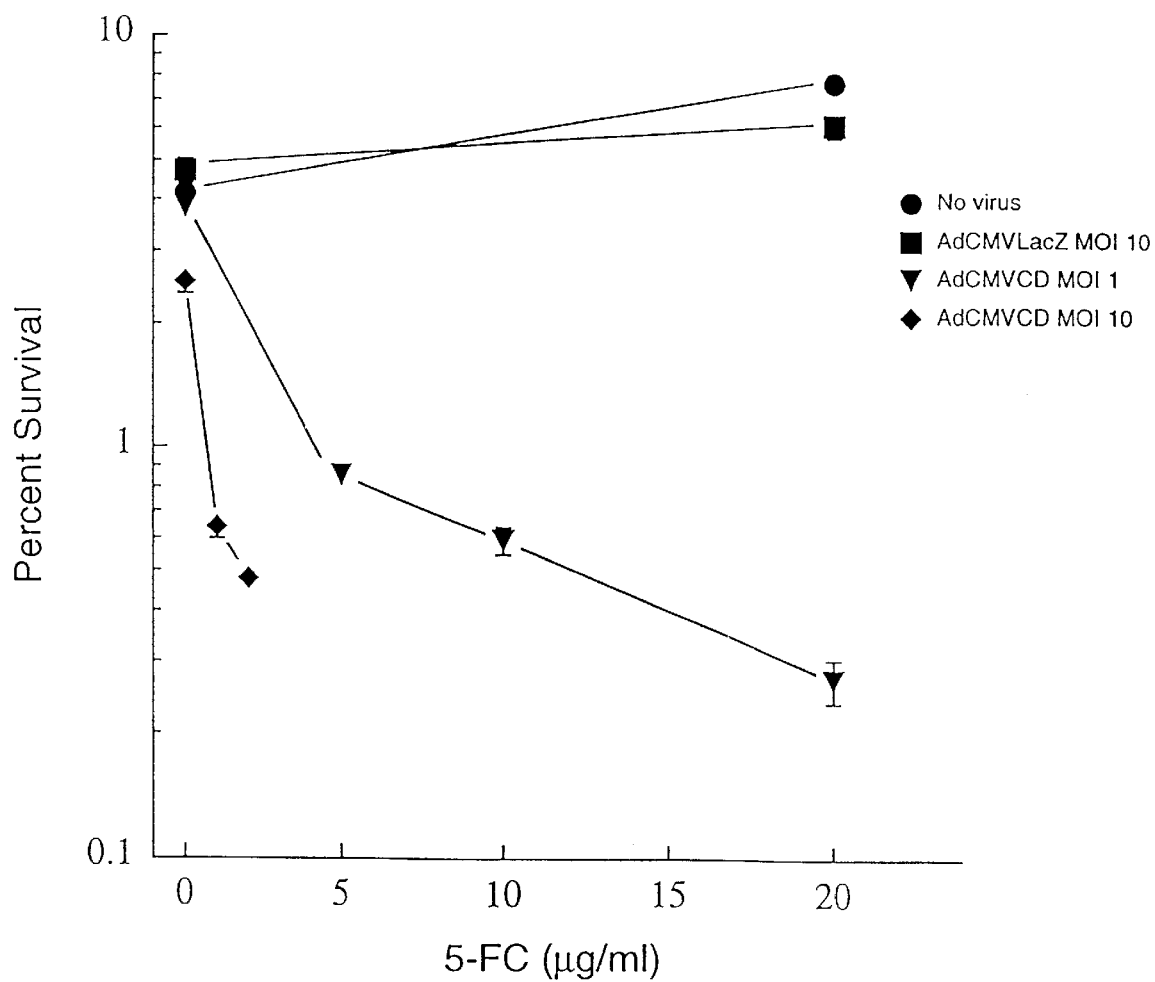
FIG. 2 shows survival of WiDr cells at 8 Gy following infection with AdCMVCD at MOIs of 1 and 10. Uninfected and AdCMVLacZ infected WiDr cells with and without 5-FC served as controls. Cells were exposed to 5-FC for 3 days prior to irradiation and plating for colony formation. The values represent the mean of 2–6 experiments done in triplicate determinations for each condition. Error bars represent the standard error of the mean.

Whether expression of cytosine deaminase with 5-FC treatment would enhance radiation cell killing at a single dose of radiation in WiDr cells was then determined. AdCMVCD and 5-FC concentrations giving at least 90% killing alone were used in the radiation survival experiments. Percent survival following a single 8 Gy radiation dose following AdCMVCD infection at 1 and 10 MOI with increasing 5-FC concentrations was determined for WiDr cells (FIG. 2). An enhanced radiation cytotoxicity was observed with increasing 5-FC concentrations at each MOI tested. The maximal radiation enhanced cytotoxicity was observed at 1 and 10 MOI with 20 and 2 μg/ml 5-FC, respectively.

Figure 3:
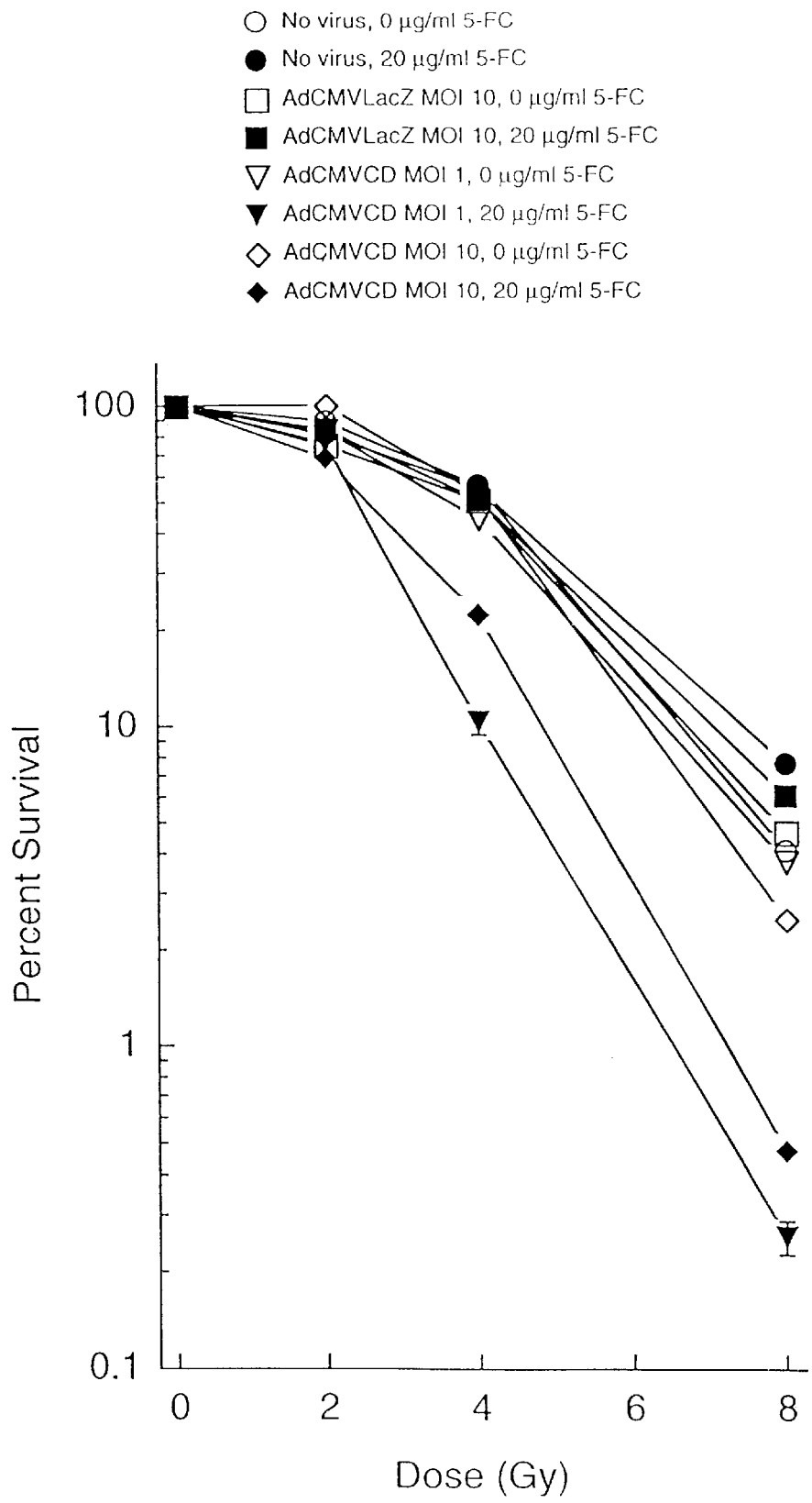
FIG. 3 shows radiation dose response for WiDr cells infected with AdCMVCD at MOIs of 1 and 10 and exposed to 5-FC for 3 days prior to irradiation. Uninfected and AdCMVLacZ infected WiDr cells with and without 5-FC served as controls. The values represent the mean of 2–6 experiments done in triplicate determinations for each condition. Error bars represent the standard error of the mean.

The conditions that gave the greatest radiosensitization at 8 Gy were identified for WiDr and used to establish a dose response relationship (FIG. 3). The greatest increase in cell killing was observed with 1 MOI and 20 µg/ml of 5-FC. The radiation survival curve parameters calculated using the linear quadratic and single hit multiple target (SHMT) models are listed in Table 1. Only the two AdCMVCD groups with 20 or 2 µg/ml 5-FC had non zero α values (0.221 and 0.065 for 1 and 10 MOI, respectively). The β values were similar for all groups. For the SHMT model, the lowest $D_0$ values were for the AdCMVCD groups with 5-FC (0.990 and 1.034 for 1 and 10 MOI, respectively). However AdCMVCD, 10 MOI without 5-FC had a low $D_0$ of 1.177 compared to the range of the other groups of 1.338–1.760. Additionally, the lowest $D_q$ values were obtained for the AdCMVCD groups with 5-FC (1.952 and 2.569 for 1 and 10 MOI, respectively) while the values for the other groups ranged from 3.207–3.825.

TABLE 1

Radiobiologic parameters of in vitro survival curves for human colon cancer cell line WiDr infected with AdCMVCD, AdCMVLacZ or no viral infection, treated with 5-FC and exposed to $^{60}$Co radiation.

| Treatment Group | Linear Quadratic Parameters | | | | Single Hit Multiple Target Parameters | | |
|---|---|---|---|---|---|---|---|
| | α | β | α/β | $r^2$ | $D_o$ | $D_q$ | $r^2$ |
| No Viral Infection, 0 µg/ml 5-FC | 0 | 0.050 | 0 | 0.993 | 1.338 | 3.825 | 0.999 |
| No Viral Infection, 20 µg/ml 5-FC | 0 | 0.040 | 0 | 0.999 | 1.760 | 3.679 | 0.998 |
| AdCMVLacZ, 10 MOI, 0 µg/ml 5-FC | 0 | 0.047 | 0 | 0.996 | 1.502 | 3.614 | 0.993 |
| AdCMVLacZ, 10 MOI, 20 µg/ml 5-FC | 0 | 0.044 | 0 | 1.00 | 1.673 | 3.459 | 0.999 |
| AdCMVD, 1 MOI, 0 µg/ml 5-FC | 0 | 0.051 | 0 | 1.00 | 1.496 | 3.207 | 0.999 |
| AdCMVD, 1 MOI, 20 µg/ml 5-FC | 0.221 | 0.069 | 3.211 | 0.979 | 0.990 | 1.952 | 0.996 |
| AdCMVD, 10 MOI, 0 µg/ml 5-FC | 0 | 0.059 | 0 | 0.988 | 1.177 | 3.674 | 1.00 |
| AdCMVD, 10 MOI, 2 µg/ml 5-FC | 0.065 | 0.076 | 0.851 | 1.00 | 1.034 | 2.569 | 0.998 |

Figure 4:
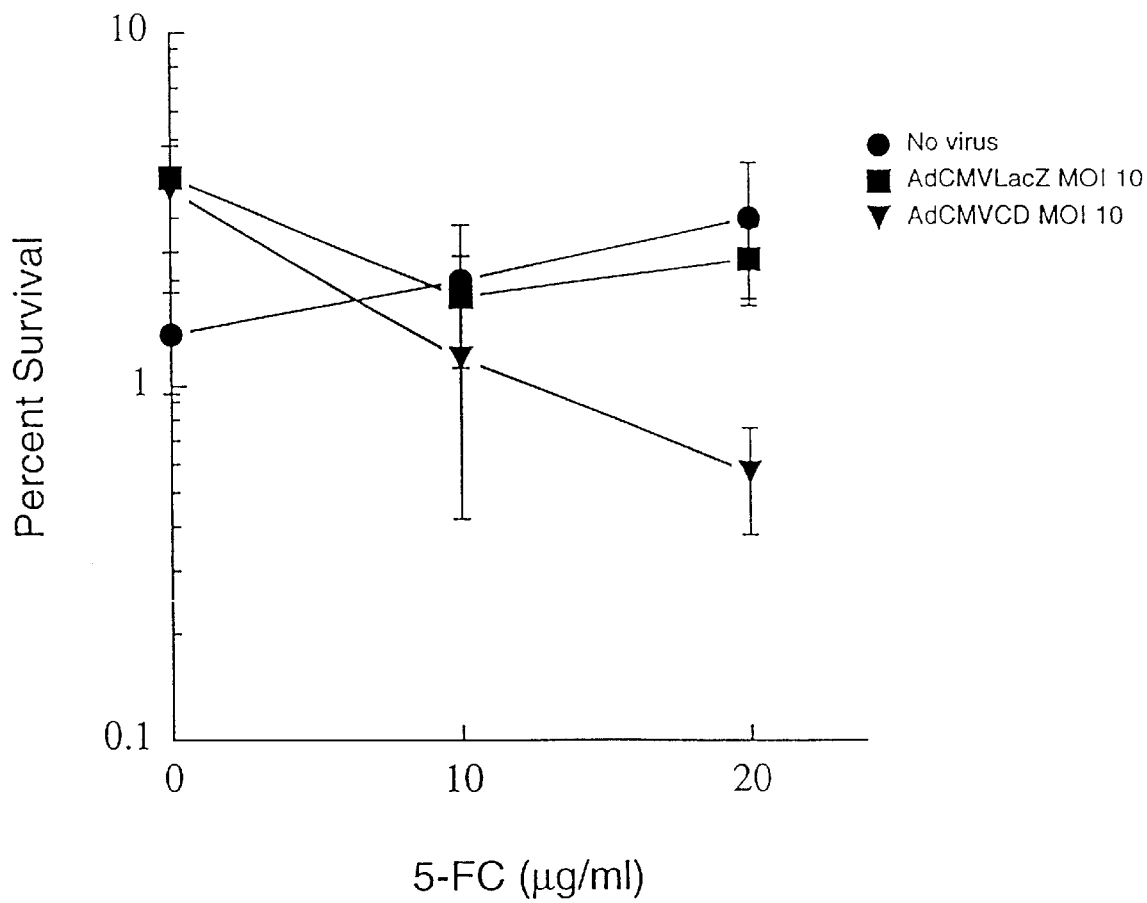
FIG. 4 shows survival of SK-ChA-1 cells following infection with AdCMVCD at an MOI of 10, treated with 5-FC and 8 Gy radiation. Uninfected cells and AdCMVLacZ infected SK-ChA-1 cells with and without 5-FC served as controls. Cells were exposed to 5-FC (0, 10 or 20 μg/ml) for 3 days prior to irradiation and plating for colony formation. The values represent the mean of 6 replicates in 2 separate experiments. Error bars are the standard error of the mean.

The radiation induced killing of SK-ChA-1 cells treated with ADCMVCD infection, 5-FC, and 8 Gy radiation is illustrated in FIG. 4. The enhanced effects of combined treatment were most evident at the 20 µg/ml dose of 5-FC. A detailed radiation dose response analysis was published in Table 1 of Pederson et al. (14). These prior studies demonstrated a $D_0$=0.968 and α=0.444 for the combined modality treatment of the SK-ChA-1 cholangiocarcinoma cells. The large value of α and small $D_0$ indicate significant reduction in cell survival as a result of the combined treatments with low (2 Gy) and high (8 Gy) single fraction radiation exposures. A similar trend was observed in the radiation survival parameters obtained using the WiDr colon cancer cells (Table 1). The largest α values and smallest $D_0$ values were observed for the AdCMVCD infected cells treated with 5-FC.

Figure 5A:
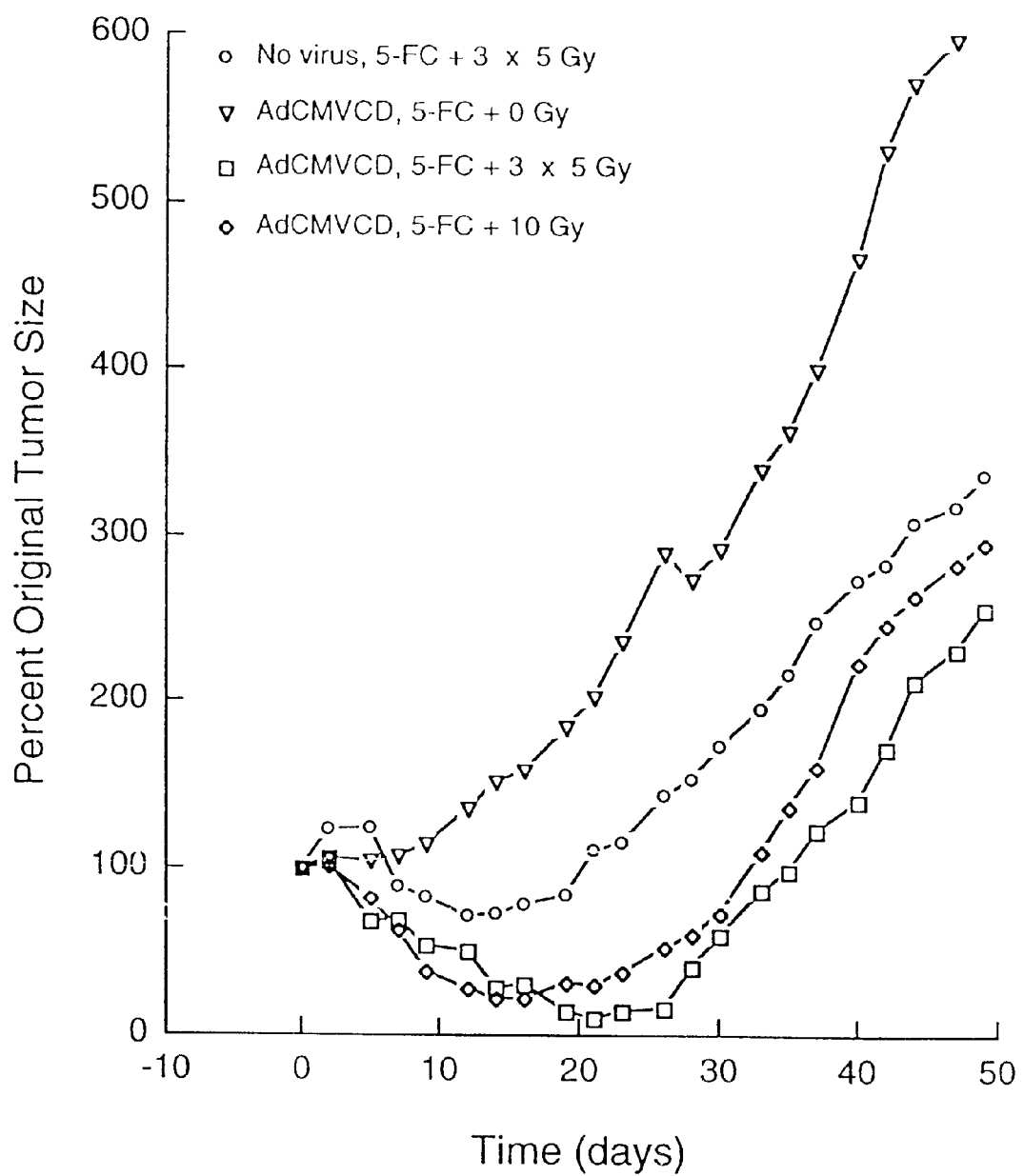
FIG. 5A shows growth of WiDr colon carcinoma tumor nodules treated with AdCMVCD, 5-FC and $^{60}$Co radiation. Mice received $2\times10^7$ WiDr cells by s.c. injection, and tumors with diameters of 5–10 mm formed in 7 days. At this time, three injections of AdCMVCD ($1\times10^9$ pfu) were administered intratumorally on days –2, 0, and 2 relative to radiation treatment on day 0. All animals received 5-FC (500 mg/kg twice daily by i.p. injection) beginning on day –2 for 7 days. The radiation treatment groups received 10 Gy $^{60}$Co (day 1) or 5 Gy (days 0, 1, and 2) to their tumor. Data points represent the mean change in tumor surface area relative to day 0 for groups of animals (n=6).
Figure 5B:
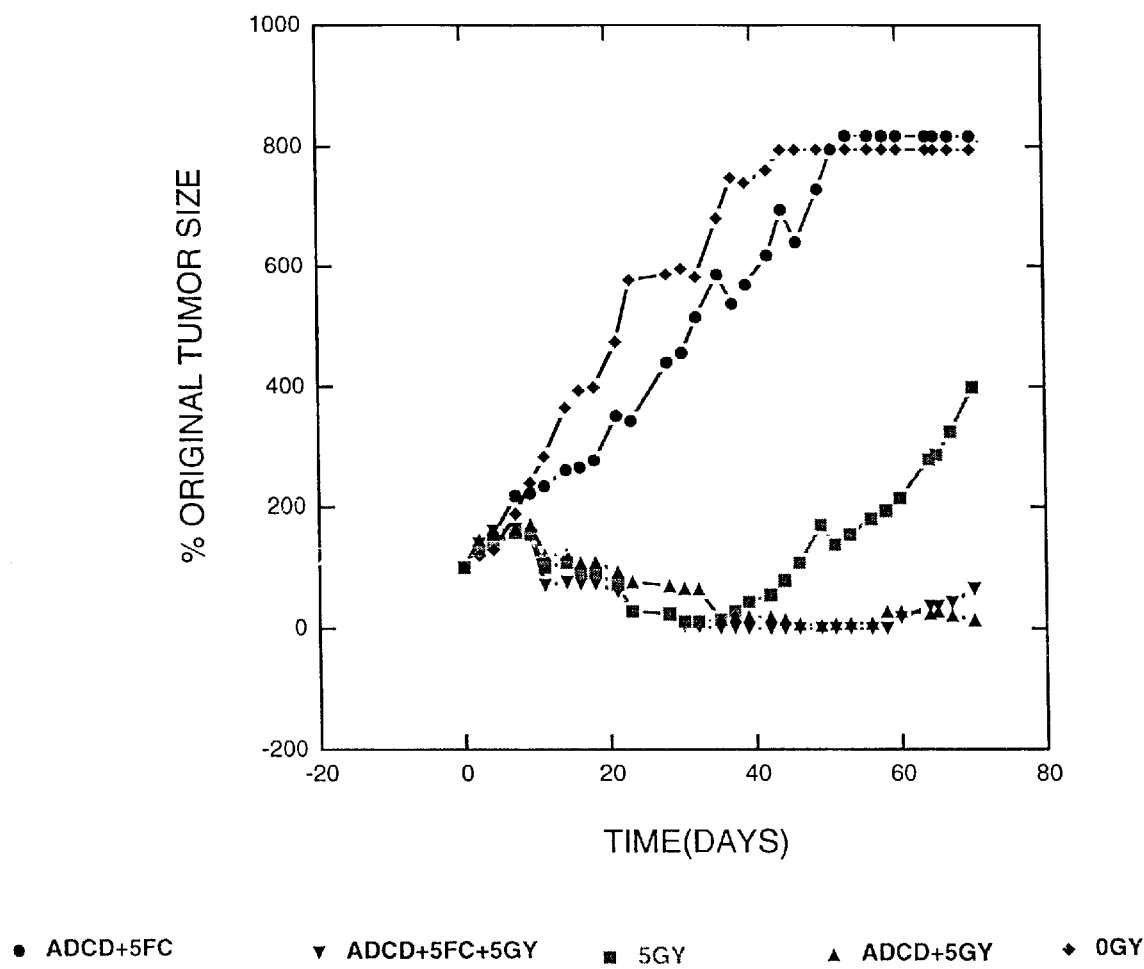
FIG. 5B shows growth of WiDr colon carcinoma tumor nodules treated with AdCMVCD, 5-FC and $^{60}$Co radiation. Mice received $2\times10^7$ WiDr cells by s.c. injection, and tumors with diameters of 5–10 mm formed in 7 days. At this time, three injections of AdCMVCD ($1\times10^9$ pfu) were administered intratumorally on days –2, 0, and 2 relative to radiation treatment on day 0. One week later, the AdCMVCD injections were repeated. All animals received 5-FC (500 mg/kg twice daily by i.p. injection) beginning on Day –2 for 14 days. The radiation treatment groups received 5 Gy (days 0, 1, 2, 7 and 8) to their tumor. Data points represent the median change in tumor surface area relative to day 0 for groups of animals (n=10).

To establish the efficacy of cytosine deaminase and 5-FC with radiation therapy for WiDr cells in vivo, subcutaneous WiDr tumors were established in the flanks of athymic nude mice. The irradiation conditions included a single 10 Gy dose or 3×5 Gy fractions on 3 consecutive days. Two mice from each combination therapy group died from the treatment. Tumor growth was measured and the change in tumor size determined over time. Two of 6 tumors in the combined AdCMVCD+5-FC+3×5 Gy modality group regressed but subsequently recurred, while 3 of 6 tumors regressed then recurred in the 10 Gy combined modality group. The AdCMVCD+5-FC+10 Gy and the AdCMVCD+5-FC+3×5 Gy groups produced the longest times to tumor regrowth and tumor doubling, but were not significantly different from each other. The AdCMVCD+5-FC+10 Gy, AdCMVCD+5-FC+3×5 Gy and the 5-FC+3×5 Gy groups all had significantly longer times to tumor doubling (FIG. 5) than the AdCMVCD+5-FC+0 Gy group (P=0.0037, 0,01, and 0.0006, respectively) as well as significantly longer times to tumor regrowth (P=0.001, 0.0026, and 0.001, respectively). Both the AdCMVCD+5-FC+10 Gy and the AdCMVCD+5-FC+3×5 Gy groups had significantly longer times to tumor regrowth than the 5-FC+3×5 Gy group (P=0.0103 and 0.0153, respectively) (FIG. 5A). The 5-FC+3×5 Gy and the AdCMVCD+5-FC treated groups were not significantly different. No other significant pairwise differences existed in time to tumor regrowth or doubling. Tumor growth was inhibited for a longer period with AdCMVCD+5-FC+5×5 Gy (FIG. 5B).

Figure 6:
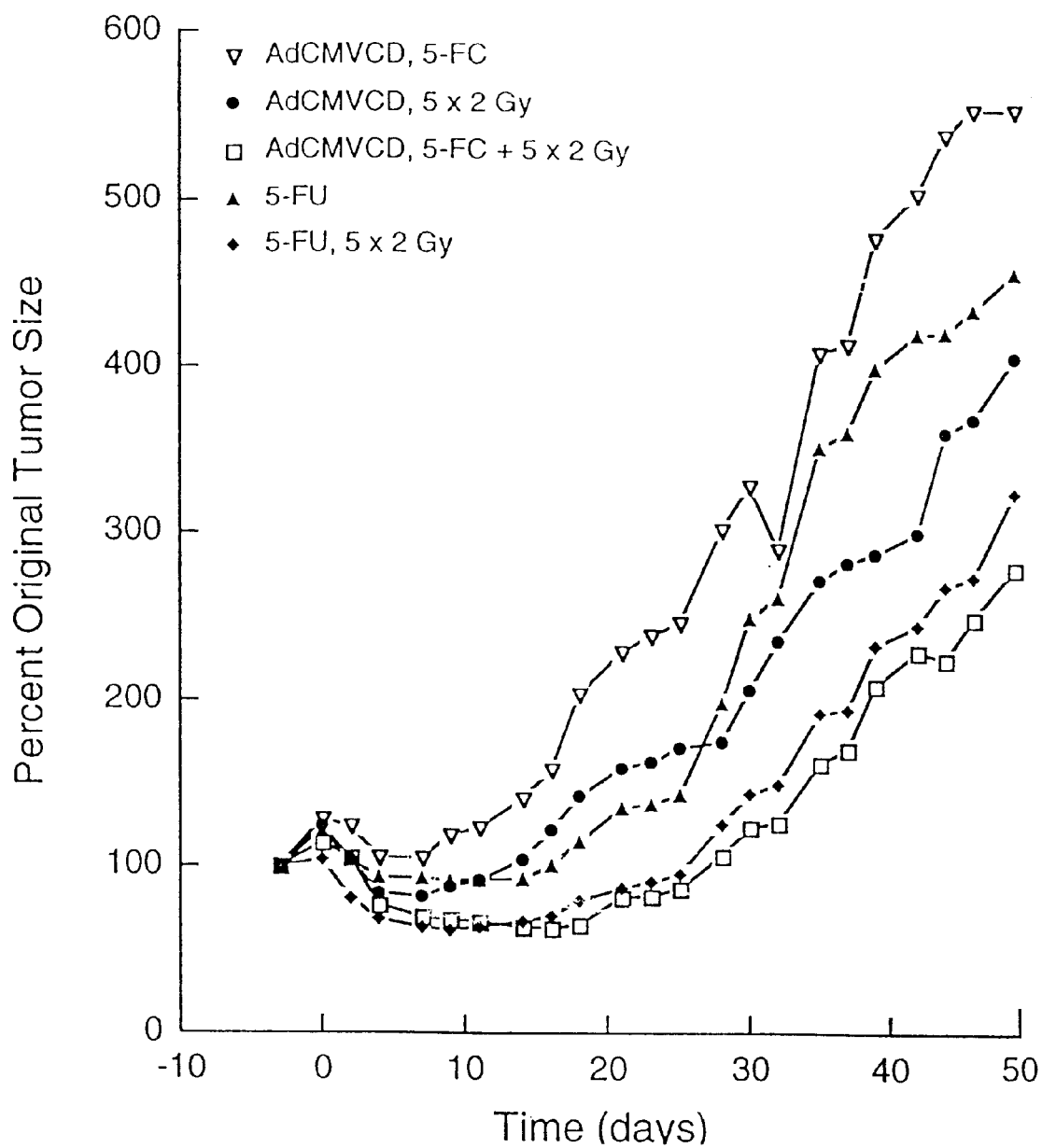
FIG. 6 shows growth of SK-ChA-1 cholangiocarcinoma tumors treated with AdCMVCD, 5-FC, and 5×2 Gy $^{60}$Co radiation. Controls included 5-FU with and without radiation, AdCMVCD+5-FC, and no treatment. Mice received $2\times10^7$ SK-ChA-1 cells by s.c. injection, and tumors with diameters of 5–10 mm formed in 7 days. At this time, three injections of AdCMVCD ($1\times10^9$ pfu) were administered intratumorally on days –2, 0, and 2 relative to initiation of radiation treatment on day 0. Animals received 5-FC (400 mg/kg twice daily by i.p. injection) or 5-FU (15 mg/kg twice daily by i.p. injection) beginning on day –2 for 7 days. The radiation treatment group received 2 Gy $^{60}$Co (days 0–4) to their tumor. Data points represent the mean change in tumor surface area relative to day 0 for groups of animals (n=10).

The AdCMVCD+5-FC+5×2 Gy and the 5-FU+5×2 Gy groups had the longest times to SK-ChA-1 tumor regrowth, however they were not significantly different from each other (FIG. 6). No differences existed in time to tumor doubling among the treatment groups. The time to tumor regrowth did not differ between the AdCMVCD+5-FC and 5-FU alone treatment groups. The AdCMVCD+5-FC+5×2 Gy group had a significantly longer time to tumor regrowth compared to the 5-FU alone and the AdCMVCD+5×2 Gy groups (P=0.0126 and 0.0121, respectively) (FIG. 6). The 5-FU+5×2 Gy group also had a significantly longer time to tumor regrowth compared to the 5-FU alone and AdCMVCD+5×2 Gy groups (P=0.0204 and 0.0180, respectively).

The use of gene transfer methods employing adenoviral vectors to sensitize cells to the effects of ionizing radiation can be used for solid tumor therapy. An adenovirus encoding the cytosine deaminase gene used with the prodrug 5-FC can lead to enhanced cell killing when used in combination with ionizing radiation in vitro and in vivo for 2 human gastrointestinal malignancies, colon carcinoma and cholangiocarcinoma. Previous studies in human cholangiocarcinoma (14, 15) demonstrated the in vitro radiosensitizing effects of combining cytosine deaminase transgene expression with 5-FC prodrug treatment and single fraction radiation therapy. The small $D_0$ and large α values obtained for the combination treatment groups indicate cytotoxic effects both at high and low radiation doses for the WiDr cells which is similar to what occurred with the cholangiocarcinoma cells.

From the encouraging results of the in vitro evaluation of induction of radiosensitivity for both colon cancer and cholangiocarcinoma cells, in vivo models were evaluated. For SK-ChA-1 cholangiocarcinoma tumors, an enhanced anti-tumor effect was seen from combined AdCMVCD infection, 5-FC administration, and a single 10 Gy radiation dose compared to AdCMVCD infection and 5-FC alone. Radiation therapy in the clinical setting is traditionally delivered in daily 2 Gy doses over 4–6 weeks. Analysis of this format of radiation therapy and CD/5-FC gene therapy with human colon cancer and cholangiocarcinoma indicated the fractionated delivery of 3×5 Gy doses or 5×2 Gy doses was at least as effective as a single 10 Gy fraction or with systemically administered 5-FU and 5×2 Gy doses. Thus, a measurable anti-tumor effect was observed with CD/5-FC gene therapy in combination with low dose fractionated radiation therapy.

Khil et al. showed that the cytosine deaminase gene stably transfected into WiDr cells was able to enhance radiation cell killing in vitro (13). Adenoviral vectors have been used in many gene transfer and therapy studies. The use of adenoviral vectors to encode cytosine deaminase and convert 5-FC to 5-FU to achieve cell killing has been reported (25, 26). Ohwada et al. delivered a n adenoviral vector encoding cytosine deaminase into normal tissue 0.8–1 cm from the site of colon tumor xenografts in the liver of mice and systemically delivered 5-FC to suppress metastatic tumor growth (29). Therefore, there is potential that treatment of primary tumor nodules with the combination of 5-FC conversion to 5-FU by the cytosine deaminase gene and radiation could lead to increased local control while the production of 5-FU would serve to suppress metastatic growth.

Both metastatic colon carcinoma and locally advanced cholangiocarcinoma are difficult clinical problems, and have been resistant to single modality therapy (6, 30, 31). The gene therapy approach of molecular chemotherapy combined with radiation therapy provides a new approach to the treatment of solid tumors. The ability of 5-FC and 5-FU to freely diffuse across cell membranes is one advantage of the CD/5-FC toxin gene/prodrug strategy. This is in contrast to the HSVtk/GCV system where cellular gap junctions are a vital component of the bystander effect (32, 33). Another advantage of CD/5-FC demonstrated here with respect to the WiDr colon cancer model was efficacy at a very low viral concentration of 1 MOI. A MOI of 1 with a high 5-FC concentration (20 $\mu$g/ml) was more effective than a MOI of 10 and a low 5-FC concentration (2 $\mu$g/ml). This is an important observation since it may be difficult to achieve 100% infection of cells in solid tumors in situ. In vivo studies lend support to the possibility that less than 100% tumor infection can be effective. Although it is likely that only a fraction of tumor cells in the xenografts were infected, a significant regrowth delay was observed in the irradiated, AdCMVCD infected tumors treated with 5-FC compared to irradiation alone or the AdCMVCD infected and 5-FC treated tumors without irradiation. An important observation was that low dose multifraction radiation treatment in combination with CD/5-FC gene therapy was effective in inhibiting tumor growth. The ability to achieve greater regrowth delay with combined modality therapy with an adenoviral vector in vivo demonstrates the potential of this cancer gene therapy strategy as a treatment modality that can be tested in human clinical trials.

Such enzyme/prodrug strategy consisting of CD/5-FC relies on diffusion of the cytotoxic enzymatic product 5-FU to kill non-transduced tumor cells. It can be utilized in local and regional situations where the cancer is accessible for intratumor or regional injection of the cytosine deaminase vector. Tropism-modified adenovirus or an adenovirus encoding the cytosine deaminase gene under control of a tumor specific promoter may be required for selective gene delivery to disseminated metastatic cancer. However, native adenoviral tropism can be redirected through other cell surface receptors, such as fibroblast growth factor (FGF) receptor. The following examples demonstrate methods to increase gene delivery via vector binding to tumor markers. Adenovirus vector was redirected via FGF receptor for the delivery of cytosine deaminase gene to hepatobiliary tumor cells for combination of molecular chemotherapy and radiation therapy studies.

EXAMPLE 8

Cell Lines

The human cholangiocarcinoma cell lines SK-ChA-1 and Oz were gifts of Dr. A. Knuth (Ludwig Institute for Cancer Research, London, UK) and Dr. N. F. LaRusso (Mayo Clinic, Rochester, Minn.) respectively. BXPC-3, ASPC-1 and CFPAC-1 human pancreatic carcinoma cell lines were obtained from the American Type Culture Collection (ATCC CRL-1687, ATCC CRL-1682 and: ATCC CRL-1918; Rockville, Md.). SK-ChA-1, Oz and BXPC-3 cells were maintained in RPMI-1640 medium supplemented with L-glutamine (2 mM), and 10% heat inactivated fetal bovine serum (FBS) (Summit Biotechnology, Ft. Collins, Co.) at 37° C. in a humidified 5% $CO_2$ atmosphere. ASPC-1 cells were maintained in RPMI-1640 medium supplemented with L-glutamine (2 mM), and 20% FBS at 37° C. in 5% $CO_2$ atmosphere.

EXAMPLE 9

Fab-FGF2 and Fab'-FGF2 Conjugates

The recombinant adenoviral vectors (AdCMVLacZ, AdCMVLuc, and AdCMVCD) were redirected with FGF2 to the FCF receptor by utilization of a bi-specific conjugate constructed and validated as described (34). Fab-FGF2 was constructed by utilizing the 1 D6.14 anti-adenoviral knob monoclonal antibody, and production of the Fab fragment. This moiety was conjugated to human FGF2 by disulfide linkage.

To decrease the heterogeneity of the Fab-FGF2 conjugates, a Fab'-FGF2 conjugate was generated. The ascites containing the anti-knob 1D6.14 antibody was loaded onto a protein A column in phosphate buffer, pH 7.4 and eluted with 0.1 M glycine. pH 3.5. The purified IgG was digested with immobilized pepsin to obtain F(ab)'$_2$ fragments. The digestion mixture was purified by protein A chromatography and the flow-through containing the F(ab)'$_2$ was buffer exchanged by gel filtration chromatography (Sephacryl S-200, Pharmacia, Uppsala, Sweden). The purified F(ab)'$_2$ fragments were mildly reduced with 2-mercaptoethylamine-HCl. The sulfhydryl group on the Fab' fragment was activated with Ellman's reagent (DTNB) at a 1:3 molar ratio for 30 min which results in Fab'-TNB. Excess DTNB was removed by diafiltration using an Amicon stirred cell apparatus (Beverly, MA) equipped with a YM30 and then put through a 0.2 $\mu$m filter to obtain pure TNB-Fab', TNB-Fab' and FGF2 were mixed at a 1:1 molar ratio and incubated for 12–16 hours at 4° C. to generate the Fab'-FGF2 conjugate. The reaction mixture was purified by heparin affinity chromatography (Heparin Sepharose, FF, Uppsala, Sweden). Fractions containing Fab'-FGF2 were further purified by gel filtration (Sephacryl S-100 HR, Pharmacia, Uppsala, Sweden). The Fab'-FGF2 was filtered through a 0.2 $\mu$m membrane and stored at −80° C. The material was determined to be greater than 95% pure by SE-HPLC. The Fab'-FGF2 conjugate was analyzed using the anti-knob ELISA and shown to have very similar binding characteristics as the anti-knob Fab and Fab-FGF2. In addition, the materials, final product and intermediates were also characterized by SDS-PAGE under reducing and non-reducing conditions. All the materials migrated as expected and the final product was pure.

Functional validation of the conjugate moieties was defined prior to use. The Fab and Fab' moiety binding to adenoviral type 5 knob protein was confirmed by ELISA. Functional ability of the FGF2 moiety of the conjugate was evaluated using a bovine aortic endothelial cell proliferation assay. The Fab-FGF2 and Fab'-FGF2, when complexed with Ad5, showed comparable levels of gene expression when assayed on SKOV3.ip1 cells. Fab-FGF2 was used in the majority of the in vitro studies and the in vivo study utilized the Fab'-FGF2 as the retargeting moiety.

EXAMPLE 10

Recombinant Adenoviruses

E1A deficient replication-incompetent serotype 5 adenoviral vectors were used to analyze Fab-FGF2 and Fab'-FGF2 redirected adenoviral gene transfer. AdCMVLuc encodes the firefly luciferase gene under the control of the human cytomegalovirus (CMV) promoter/enhancer, and has been described (35). AdCMVLacZ contains the LacZ reporter gene and induces expression of the *E. coli* β-galactosidase enzyme under control of the CMV promoter (35). AdCMVCD encodes the *E. coli* cytosine deaminase gene under control of the CMV promoter, and was constructed, functionally validated, and propagated as described (14).

EXAMPLE 11

Redirected Marker Gene Adenoviral Infections

Either AdCMVLuc or AdCMVLacZ was incubated with Fab-FGF2 conjugate in a volume of 130 μl at room temperature for minutes. Dilutions of this stock to varying plaque forming units (pfu) of virus were made and then added to 30,000 cells/well in a 12 well dish (Costar, Cambridge, Mass.) and incubated at 37° C. for 2 hours. Infections were terminated by addition of 5 ml of complete media.

EXAMPLE 12

Analysis of AdCMVLuc and AdCMVLacZ Gene Expression

Luciferase assays were performed according to the manufacturer's instructions 24 hours after infection (Luciferase Assay Kit, Promega, Madison, Wis.). Briefly, cell lysates from infected cells were obtained by aspirating culture media, washing cells with PBS, and adding 150 μl of cell lysis buffer to each well. Cells were lysed at room temperature for 10 minutes and cellular debris removed by refrigerated centrifugation at 13,000×g for 5 minutes. Assay reagent was added to the cell lysates and analyzed for emitted light on a luminometer (Lumat, Berthold, Nashua, N.H.).

To analyze AdCMVLacZ gene expression, in brief, 48 hours following infection cells were fixed in 12-well dishes (Costar) with 0.5% glutaraldehyde (Sigma). The cells were washed with PBS, and stained with X-gal 5-bromo-4-chloro-3-indolyl-β-D-galactoside substrate with 2 mM MgCl$_2$, 5 mM K$_3$Fe(CN)$_6$, and 0.3% Nonidet P-40 (Sigma).

EXAMPLE 13

In Vitro Adenoviral Infections for Fab-FGF2 Redirection of Reporter Gene Expression and Measurement of Reporter Gene Expression Cells were plated at a density of 4×104 per well in 12-well culture dishes and infected with recombinant adenovirus (AdCMVLacZ or AdCMVLuc) or adenovirus+Fab-FGF2 conjugate 24 hours later. The adenovirus and Fab-FGF2 conjugate were mixed in a volume of 130 μl at room temperature, and allowed to incubate for 30 minutes prior to infection of the cell monolayers. Cellular infections were carried out in a minimal volume (0.5 ml) of Optimem (Gibco BRL, Grand Island, N.Y.) for 2 hours at 37° C., then 5 ml of complete medium added.

The luciferase kit from Promega was used according to manufacturer's recommendations. Cells were lysed, and the cell lysates assayed for luciferase activity using a Berthold luminometer (Nashua, N.H.). Bradford protein assay was used to quantitate the protein in the samples. The data is reported as relative light units (RLU)/μg protein and is the average of 3 independent experiments.

EXAMPLE 14

Detection of Cytosine Deaminase Protein in AdCMVCD and AdCMVCD+Fab-FGF2 Infected Cells Five cell lines, SK-ChA-1, BXPC-3, Oz, CFPAC-1 and ASPC-1 were transfected as described with various MOI AdCMVCD and AdCMVCD+Fab-FGF2. Proteins were isolated from cells using Triton X-100 solubilization buffer (1% Triton X-100, 50 mM Hepes pH 7.5, 150 mM NaCl, 1.5 mM MgCl$_2$, 1 mM EDTA, 200 μM sodium orthovanadate, 10 mM sodium pyrophosphate, 100 mM sodium fluoride, 1 mM PMSF, 10% glycerol). Proteolytic inhibitors were added (aprotinin and leupeptin at a concentration of 10 μg/ml). The sample preparations with isolation buffer were incubated 10 minutes on ice, microfuged at 12,000×g for 15 minutes at 4° C., and the supernatant was collected.

Cytosine deaminase was separated by sodium dodecylsulphate-polyacrylamide gel electrophoresis (SDS-PAGE) as described by Laemmli and the samples were run under reducing conditions. Protein concentrations of the solubilized preparation were determined using the Pierce BCA protein assay kit and equal concentrations of total protein were loaded onto each lane of the gel. Rainbow colored protein weight markers (Amersham, Arlington Heights, Ill.) also were loaded onto one lane of each gel.

Proteins were electro-transferred to nitrocellulose membranes as described by Towbin et al. (36) for 12–15 hours at 0.1 amp and 1 hour at 1 amp. Membranes were .placed in milk block buffer pH 7.5 (10% powdered mild, 0.02% Nonidet P-40, 0.15 M NaCl, 0.02 M Tris) overnight at 4° C. Membranes were then incubated overnight at 4° C. with a monoclonal antibody specific for CD(37) at 5 μg/ml. The blots were rinsed, and a goat anti-mouse IgG conjugated to alkaline phosphatase was added at a concentration of 0.5 μg/ml for 1 hour to bind the primary antibody. After rinsing, an alkaline phosphatase color development kit (BioRad, Hercules, Calif.) was used to visualize the antigen-antibody reaction.

EXAMPLE 15

In Vitro Evaluation of AdCMVCD vs. AdCMVCD+Fab-FGF2 Mediated Cellular Cytotoxicity SK-ChA-1 and BXPC-3 cells were plated at 1.5×10 cells per well in 6-well plates and infected 24 hours later at a confluency of 80% with AdCMVLacZ, AdCMVCD or AdCMVCD+Fab-FGF2. Twenty-four hours later, cells were trypsinized, counted, and plated (5,000 cells/well) in 96-well microtiter plates (Costar) in 6 replicates. Media was supplemented with 5 μg/ml 5-FC (Sigma). Cell proliferation was determined by colorimetric assay (CellTiter 96 AQueous non-radioactive cell proliferation assay kit, Promega) after various periods of incubation. This assay measures the conversion of a tetrazolium salt (MTS) to formazan by viable cells. The absorbance at 490 nm was then measured in a 96-well plate reader (Molecular Devices, Menlo Park, Calif.). Data collected by the plate reader was analyzed by the SOFTmax software package (Emax Molecular Devices, Menlo Park, Calif.).

EXAMPLE 16

In Vitro Evaluation of Effectiveness of AdCMVCD vs. AdCMVCD+Fab-FGF2 Induction of CD Expression The relative expression of functional cytosine deaminase enzyme and its conversion of [6-$^3$H]-5-FC to [6-$^3$H]-5-FU was evaluated for cells infected with AdCMVCD or AdCMVCD+Fab-FGF2 using a modification of the procedure described, by Haberkorn et al. (38). SK-ChA-1 or BXPC-3 cells were plated at 1.5×106 cells per well in 6-well plates (Costar) and infected 24 hours later at a confluency of 80% with AdCMVLacZ, AdCMVCD, and AdCMVCD+ Fab-FGF2 at various viral plaque forming units (pfu). Twenty-four hours later, cells were harvested and lysed by 4 freeze-thaw cycles in 100 mM Tris-HCl, 1 mM EDTA/ dithiothreitol (Sigma), pH 7.8. Cellular debris was pelleted by centrifugation at 14,000 rpm for 5 minutes. The cytosolic fraction was separated, and 6–10 μg of cytosolic protein was incubated with (0.5 μCi) [6-$^3$H]-5-FC (Sigma) at 37° C. for 6 hours. Each reaction mixture plus 5-FU and 5-FC standards were then spotted on a cellulose thin layer chromatography plate (Eastman Kodak, Rochester, N.Y.) and developed in a butanol-water chamber. Each region (5-FU and 5-FC) was visualized under UV light, and respective areas cut from the plate and placed in 5 ml EcoLume scintillation fluid (ICN, Costa Mesa, Calif.). Each region was counted for radioactivity in a Packard Tri-Carb 1900 TR liquid scintillation counter. The [$^3$H] gate (0–18.6 keV) was utilized, with a counting efficiency of 60%. Percent conversion of 5-FC to 5-FU was calculated as activity in the 5-FU fraction compared to the total counts in the 5-FC and 5-FU fractions for each treatment condition.

EXAMPLE 17

Evaluation of AdCMVCD vs. AdCMVCD+Fab'-FGF2 in Combination with 5-FC Prodrug Administration and External Beam Radiotherapy for Induction of Anti-Tumor Response in a Nude Mouse Model of BXPC-3 Pancreatic Carcinoma The utility of FGF2 retargeting of AdCMVCD for augmentation in efficacy of this approach was evaluated. Female athymic nude mice (National Cancer Institute Frederick Research Laboratory, Frederick, Md.) were injected s.c. with 2×10$^7$ BXPC-3 cells in 50 μl PBS in both flanks. Tumors with diameters of 7 to 10 mm developed in 7 days. On Day −2 relative to radiation treatment, right sided tumors were injected with AdCMVCD+Fab'-FGF2 at 2×10$^7$ pfu in a 50 μl volume, using a 27-gauge needle, and left sided tumors were injected with 2×10$^7$ pfu of AdCMVCD. Animals were administered 5-FC at 400 mg/kg twice daily by i.p. injection beginning on Day −2 relative to radiation and continuing for 7 days. On Day 0, animals were anesthetized with 2 mg ketamine (Phoenix Scientific Inc., St. Joseph, Mo.) by i.p. injection and treated with 5 Gy $^{60}$Co radiation (80 cGy/min) with a Picker C-9 80 cm isocenter clinical irradiator (Cleveland, Ohio). Tumor diameters were measured blinded with a Vernier caliper 3 times weekly and the surface area (product of length×width) calculated. Animals were maintained in a laminar flow room under sterile conditions and fed sterilized mouse chow and tap water in accordance with University of Alabama Animal Research guidelines.

EXAMPLE 18

Statistical Analysis

A two factor analysis of variance with interaction was used to assess the effects of AdCMVLuc and AdCMVLuc+ Fab-FGF2 MOI on RLU for each of the cell types individually. Due to the nonconstant variability, the logarithm of RLU was analyzed. This transformation stabilized the variability and normalized the errors. A three-factor with interaction analysis of variance was used to assess the effects of MOI, virus type and day on the number of cells per well. Due to the nonconstant variability, the logarithm of cells per well was analyzed. This transformation stabilized the variability and normalized the errors. Global comparisons were done at the 5% significance level and all pairwise comparisons were done at the 1% significance level. A nonlinear model was used to calculate the 5-FU IC$_{50}$ for each cell type individually. The nonlinear model is given by: number of cells=trough+(peak-trough)/(1+dose/IC$_{50}$). To assess the correlation of the number of cells per well with 5-FU production, a simple linear regression was done modeling the logarithm of cells per well as a function of percent 5-FU production for each cell and virus type combination individually. Kaplan-Meier estimates on the difference in time to tumor size doubling was used to assess the difference in tumor growth in animals treated with AdCMVCD or AdCMVCD+Fab'-FGF2 plus 5-FC and radiation.

EXAMPLE 19

Determination of Firefly Luciferase Expression in Pancreatic and Cholangiocarcinoma Cells with a Redirected Ade noviral Vector Analysis of infectivity of SK-ChA-1 cholangiocarcinoma cells and BXPC-3 pancreatic carcinoma cells mediated by Fab-FGF2 redirection of AdCMVLuc was performed, and the results are shown (FIG. 7). SK-ChA-1 and BXPC-3 cells were transduced with 1, 10 and 100 MOI AdCMVLuc. An order of magnitude improvement in luciferase gene expression was observed with redirection of AdCMVLuc infection with Fab-FGF2 in SK-ChA-1 cholangiocarcinoma cells and BXPC-3 pancreatic carcinoma cells. This augmented gene delivery was blocked by pre-incubation of the conjugated virus with excess anti-FGF2 antibody. Thus, the results demonstrate increased adenovirus mediated gene delivery via the FGF2 ligand to these cells.

EXAMPLE 20

Figure 8B:
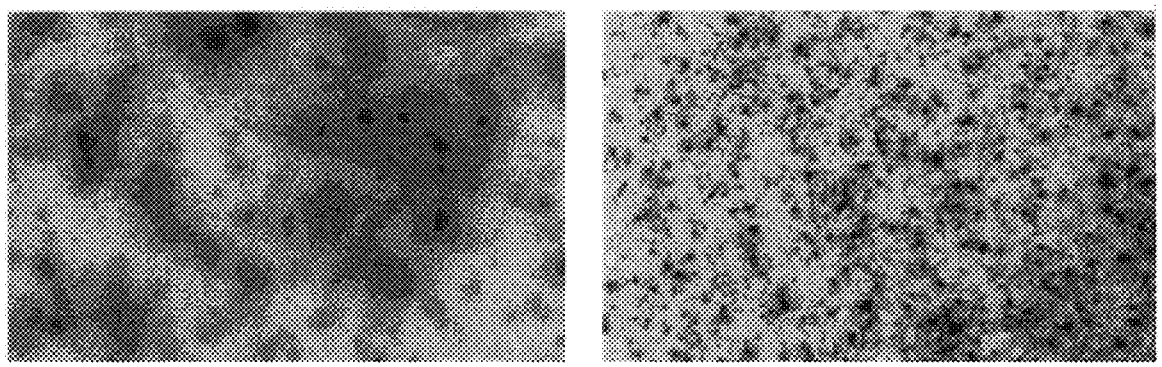
FIG. 8B shows BXPC-3 and SK-ChA-1 cells infected with AdCMVLacZ+Fab-FGF2. Redirection of AdCMVLacZ via the Fab-FGF2 moiety augmented the number of cells expressing β-galactosidase for both BXPC-3 and SK-ChA-1 cells.
Figure 9A:
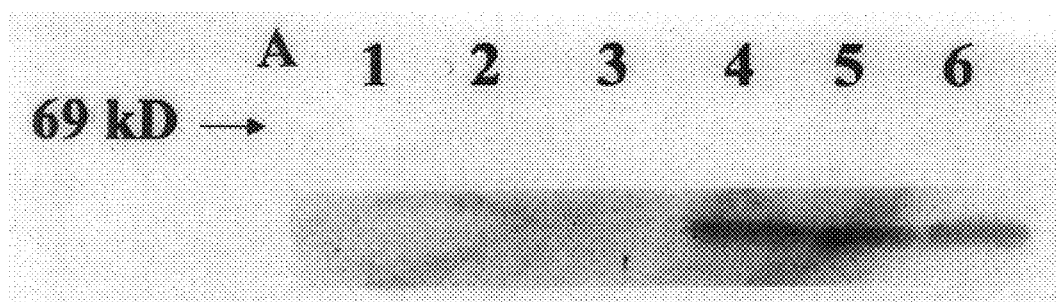
(FIG. 9A) Cell line SK-ChA-1: 1. 0 MOI (i.e., no transfection); 2. AdCMVLacZ-100 MOI; 3. 10 MOI; 4. 10R MOI; 5. 100 MOI; 6. 100R MOI.
Figure 9B:
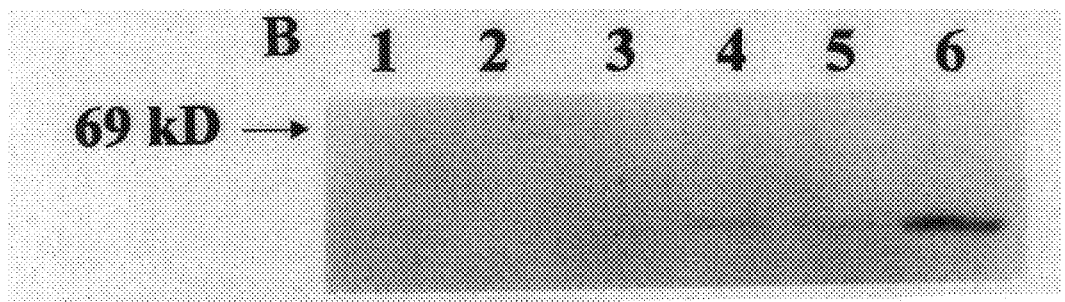
(FIG. 9B) Cell line BXPC-3: 1. 0 MOI; 2. AdCMVLacZ-10 MOI; 3. 1 MOI, 4. 1R MOI; 5. 10 MOI; 6. 10R MOI.
Figure 9C:
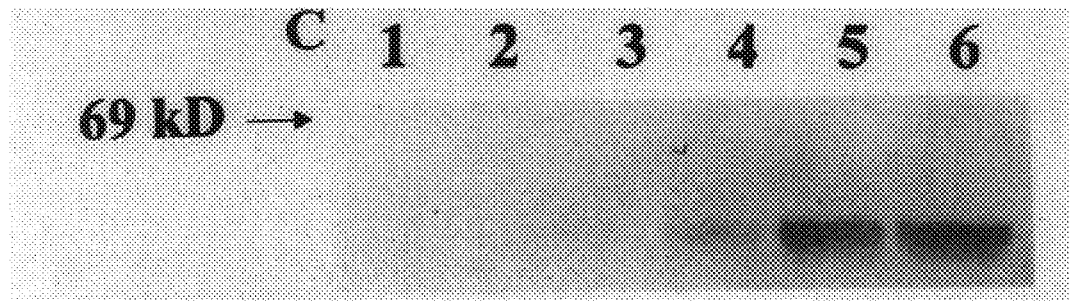
(FIG. 9C) Cell line Oz: 1. 0 MOI; 2. AdCMVLacZ-100 MOI; 3. 10 MOI; 4. 10R MOI; 5. 100 MOI; 6. 100R MOI.
Figure 9D:
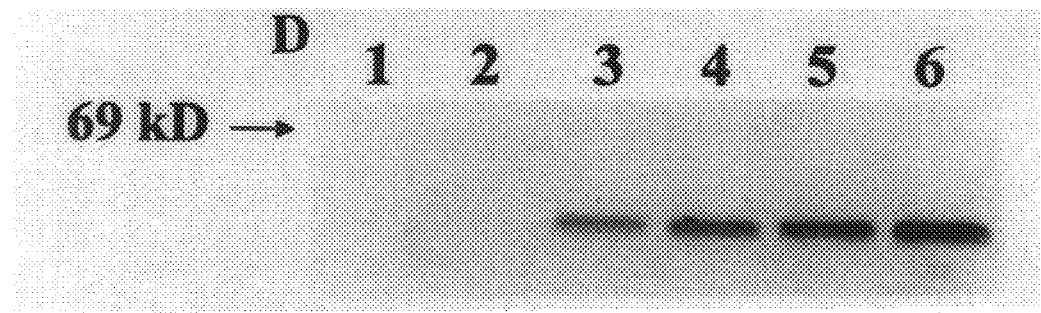
(FIG. 9D) Cell line CFPAC-1; 1. 0 MOI; 2. AdCMVLacZ-500 MOI; 3. 100 MOI; 4. 100R MOI; 5. 500 MOI, 6. 500R MOI.
Figure 9E:
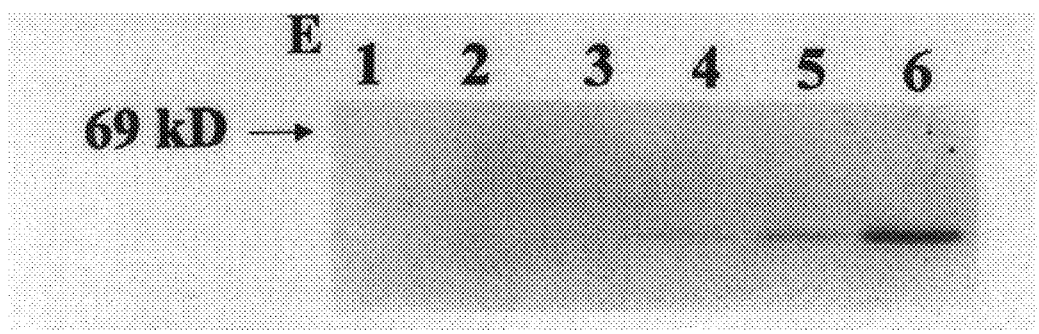
(FIG. 9E) Cell line ASPC-1; 1. 0 MOI; 2. AdCMVLacZ-100 MOI; 3. 10 MOI; 4. 10R MOI; 5. 100 MOI; 6. 100R MOI. In all cell lines, the retargeted transfection (R) with AdCMVCD+Fab-FGF2 resulted in a greater cellular concentration of CD than AdCMVCD at equivalent MOIs tested. In addition, except for the cell line SK-ChA-1 (gel A), retargeting via Fab-FGF2 induced greater CD protein with higher MOIs.

Determination of *E. coli* β-galactosidase Expression in Pancreatic and Cholangiocarcinoma Cells with a Redirected Adenoviral Vector An analysis was undertaken to visually demonstrate differential β-galactosidase expression in BXPC-3 and SK-ChA-1 cells following infection with AdCMVLacZ and AdCMVLacZ+Fab-FGF2 (FIG. 8). X-gal staining of both cell types indicated improved transduction efficiency of cells when AdCMVLacZ infection w as redirected via Fab-FGF2. LacZ gene expression was inhibited by pre-incubation of BXPC-3 and SK-ChA-1 cells with 25 μg heparin. This improved redirected transduction efficiency of cells correlated with greater luciferase gene expression (FIG. 7).

EXAMPLE 21

5-FU Cytotoxicity to Pancreatic and Cholangiocarcinoma Cell Lines

To determine the relative sensitivity of several hepatobiliary cell lines to 5-FU, the concentration of 5-FU which inhibited cellular growth by 50% (IC$_{50}$) was determined. Characterization of this information is particularly relevant to the CD/5-FC toxin gene prodrug system, as 5-FU is the toxic metabolic product of cytosine deaminase enzymatic conversion of 5-FC. The most 5-FU sensitive cell lines were CFPAC-1 and SK-ChA-1 with IC$_{50}$ values of 0.089 μg/ml and 0.115 μg/ml, respectively. BXPC-3 and ASPC-1 were less sensitive with IC$_{50}$ values of 0.134 μg/ml and 0.635 μg/ml, respectively. Thus, these results indicate that for equivalent levels of cytosine deaminase gene transfer, the various cell lines should show a differential level of 5-FU mediated cytotoxicity.

EXAMPLE 22

Determination of Differential Expression of Cytosine Deaminase in AdCMVCD and AdCMVCD+Fab-FGF2 Infected Pancreatic and Cholangiocarcinoma Cells Western blotting of cell lines transfected at various MOIs demonstrated that in all cell lines, the retargeted transfection with AdCMVCD+Fab-FGF2 resulted in a greater cellular concentration of cytosine deaminase protein than transfection with AdCMVCD alone (FIG. 9). At a higher MOI in SK-ChA-1 (FIG. 9, gel A), retargeting also generated a greater concentration of cytosine deaminase protein.

EXAMPLE 23

Figure 10A:
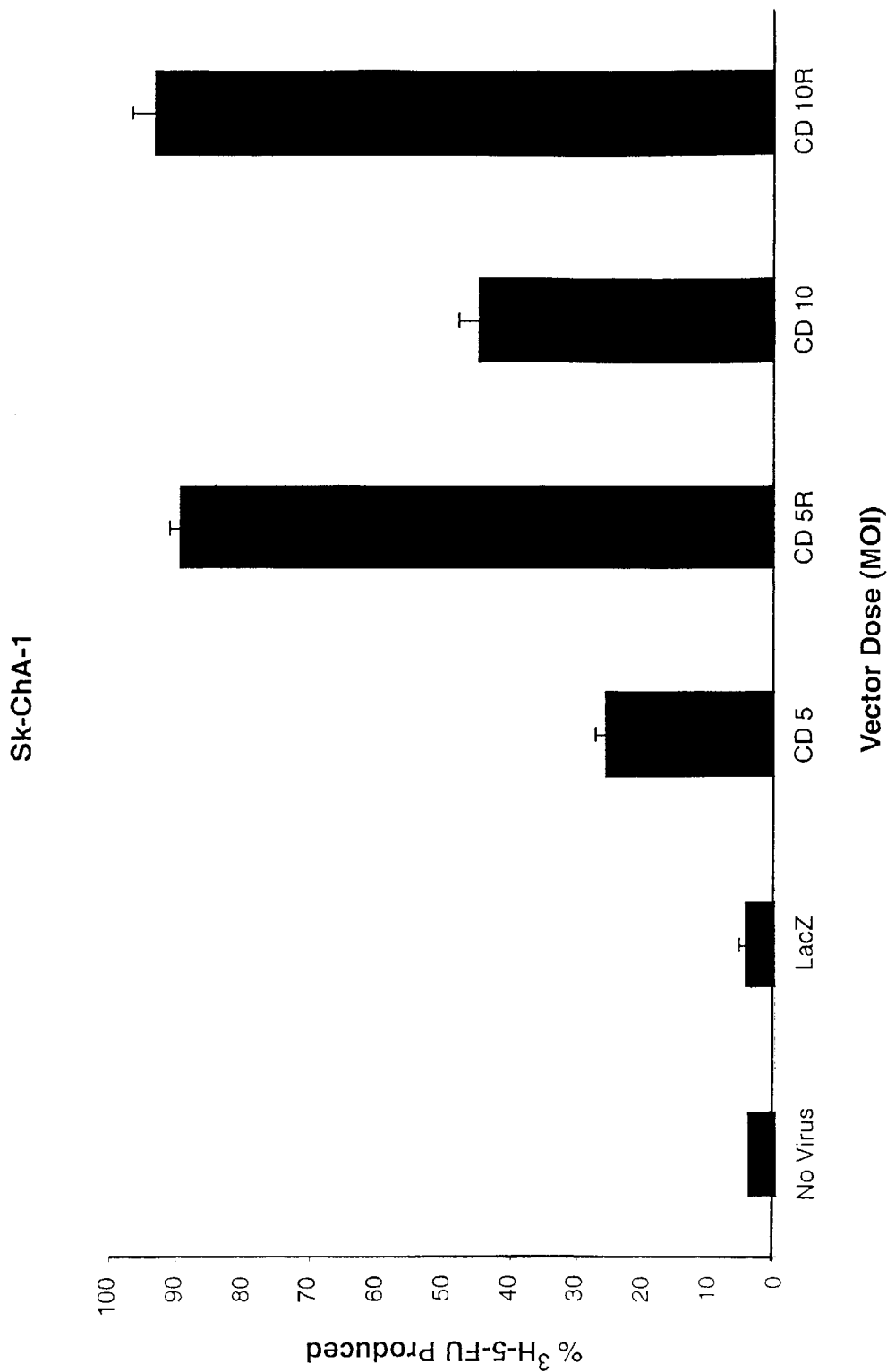
Figure 10B:
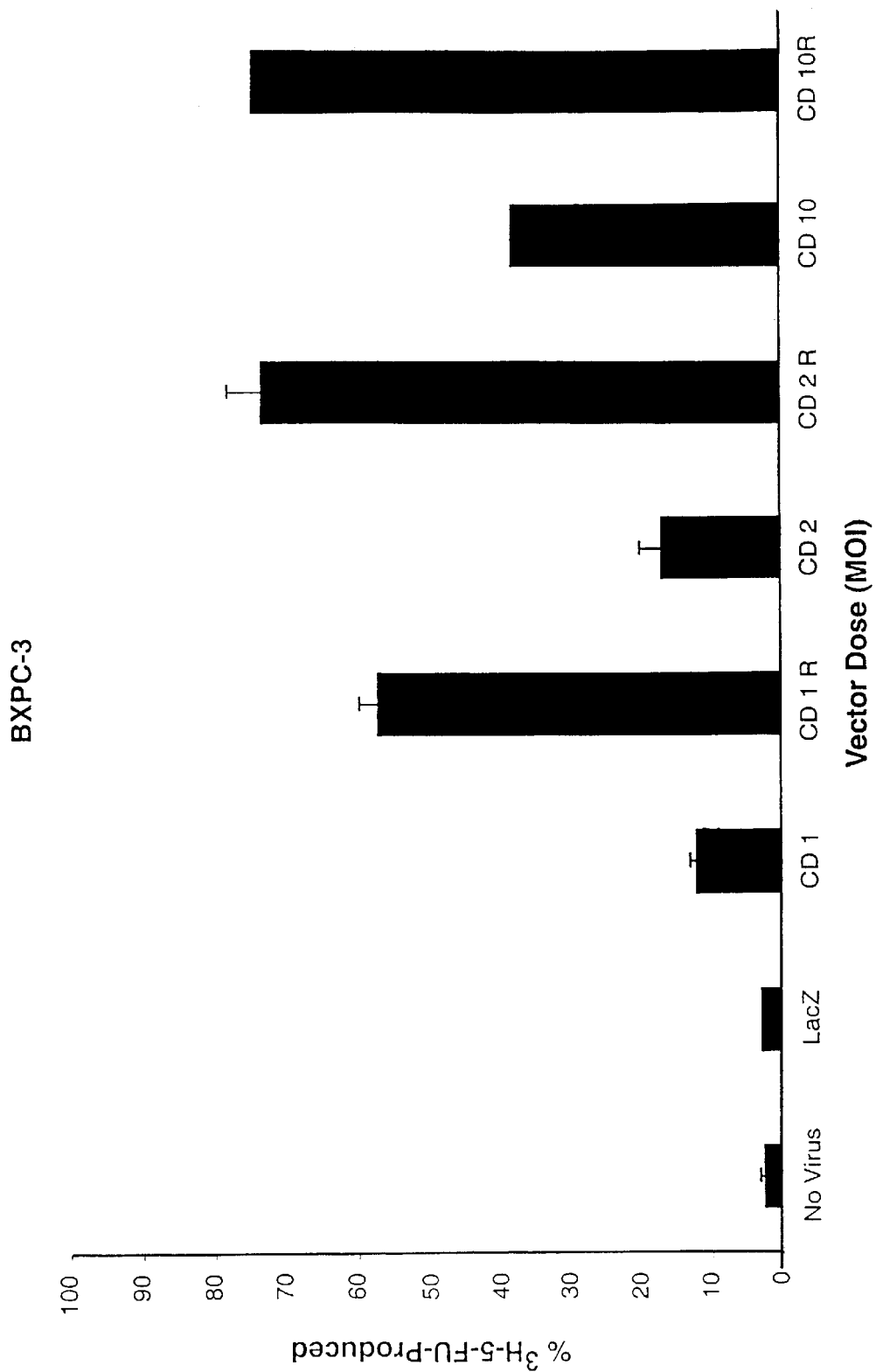

Determination of Differential Cytosine Deaminase Function in Pancreatic and Cholangiocarcinoma Cells Based upon FGF2 Redirection The relative conversion of 5-FC into 5-FU for selected hepatobiliary cell lines infected with AdCMVCD or AdCMVCD+Fab-FGF2 is shown (FIG. 10). The highest $^3$H-5-FC conversion to $^3$H-5-FU after cellular infection with 10 MOI of AdCMVCD was seen in SK-ChA-1 (44.4%), and BXPC-3 (38.4%) cells. A lower. level of conversion was seen in CFPAC-1 (6.4%) pancreatic carcinoma cells. When AdCMVCD infection was redirected by pre-incubation with Fab-FGF2, higher levels of CDenzymatic activity were observed at 10 MOI for SK-ChA-1 cells (93.5%) and BXPC-3 cells (74.8%). Similar trends were noted at 5 MOI in SK-ChA-1 cells and 1 or 2 MOI in BXPC-3 cells. For CFPAC-1 cells, increased 5-FU production via Fab-FGF2 redirection of AdCMVCD was seen in the 100 MOI group (66.9%). Cytosine deaminase mediated conversion of $^3$H-5-FC into $^3$H-5-FU was inhibited to less than 10% when AdCMVCD+Fab-FGF2 was preincubated with 25 μg heparin. Control conditions of no viral infection or control AdCMVLacZ viral infection did not result in 5-FU production, and had background levels of radioactivity (<10%). Thus, the level of 5-FC to 5-FU conversion following adenoviral retargeting compared to native adenovirus was highest at low MOI in SK-ChA-1 and BXPC-3 cell lines, while the 5-FC to 5-FU conversion rate in CFPAC-1 cells following adenoviral retargeting was high only at high MOI.

EXAMPLE 24

Determination of Differential Cytotoxicity in Pancreatic and Cholangiocarcinoma Cells Based upon FGF2 Redirection of AdCMVCD The ability of adenoviral vector redirection to enhance the sensitivity of tumors in the context of the CD/5-FC approach was evaluated. Cytotoxicity to hepatobiliary cells transduced b y AdCMVCD or AdCMVCD+Fab-FGF2 and exposed to 5 μg/ml 5-FC is shown (FIG. 11). The greatest cytotoxic effects of AdCMVCD (10 MOI) were observed in SK-ChA-1 and BXPC-3 cells. These results are consistent with the 5-FU production data (FIG. 10). SK-ChA-1 cells infected with 5, 10, or 100 MOI AdCMVCD and exposed to 5-FC for 7 days had 41.4%, 26.8% and 11.7% of cells/well relative to cells infected with 100 MOI AdCMVLacZ and exposed to 5-FC for 7 days (FIG. 11A). BXPC-3 cells infected with 1, 2, or 10 MOI AdCMVCD and exposed to 5-FC for 6 days had 73.3%, 47.7% and 19.9% of cells/well relative to cells infected with 100 MOI AdCMVLacZ and exposed to 5-FC for 6 days (FIG. 11B).

No increase in cytotoxicity was observed in the CFPAC-1 cells with increasing MOI of AdCMVCD from 5 to 100. The cell lines which converted significant amounts of 5-FC into 5-FU, had the greatest cytotoxicity following infection with AdCMVCD and exposure to 5 μg/ml 5-FC.

Cytotoxic effects induced by AdCMVCD were enhanced by pre-incubation of AdCMVCD with Fab-FGF2 prior to infection of the cells. SK-ChA-1 cells infected with 5, 10 and 100 MOI AdCMVCD+Fab-FGF2 and exposed to 5-FC for 7 days (FIG. 11A) had significantly more toxicity relative to cells infected with 5, 10 and 100 MOI AdCMVCD and exposed to 5-FC for 7 days (p=0.0001, 0.0001 and 0.0001, respectively). In BXPC-3 cells following infection with 10 or 100 MOI of AdCMVCD+Fab-FGF2 compared to AdCMVCD, retargeting with Fab-FGF2 did not result in differential cytotoxicity. The overall level of cell killing was significantly greater than no treatment controls. As BXPC-3 cells were shown to be relatively sensitive to 5-FU mediated killing with an IC$_{50}$ value of 0.134 μg/ml, the dose of AdCMVCD was decreased to 1 and 2 MOI in these cells. BXPC-3 cells transduced at these lower MOIs resulted in a differential cytotoxic effect between AdCMVCD and AdCMVCD+Fab-FGF2 infected BXPC-3 cells (p=0.0001) (FIG. 11B). In contrast, CFPAC-1 cells which did not readily convert 5-FC to 5-FU, showed induction of cytotoxicity only at 100 MOI AdCMVCD+Fab-FGF2 (p=0.0001). This data correlates with 5-FU production data (FIG. 10C).

EXAMPLE 25

In Vivo Determination of Therapeutic Efficacy of Multimodality Therapy for Established Pancreatic Tumors Utilizing Fab'-FGF2 Redirected AdCMVCD. 5-FC Administration and External Beam Radiotherapy For BXPC-3 tumors injected with AdCMVCD+Fab'-FGF2, systemic 5-FC, and external beam radiotherapy, the time to tumor doubling was extended compared to tumors injected with AdCMVCD, systemic 5-FC, and external beam radiotherapy (FIG. 12). Based on the 95% confidence interval, adenoviral retargeting extended the time to tumor doubling by 1 to 28 days.

EXAMPLE 26

Measure Tumor Cell Conversion of 5-FC to 5-FU via MRS Over Time in Human Pancreatic and Colon Cancer Cells both in vitro and in vivo In vitro models of molecular chemotherapy were developed using the AdCMVCD cytosine deaminase toxin gene for the transfection of both human pancreatic and colon cancer cell lines (BXPC-3, WiDR, LS174T). These lines when transfected with the AdCMVCD have demonstrated>75–80% cytotoxicity after the addition of 5-FC to the media. In this study, an in vitro treatment model was proposed using 3×106 BXPC-3 pancreatic tumor cells transfected at a MOI of 100 with AdCMVCD. These cells were then examined b y MRS at 0, 2, 6 and 24 hours for conversion of 5-FC to 5-FU.

Initial studies have shown the sensitivity of fluorine spectroscopy by its ability to detect 3.8 mM 5-FC when initially added to transfected BXPC-3 cells. Initial data shows that after 90 minutes, no significant change in signal intensity of the 5-FC was identified with minimal 5-FU detected. However, after 120 minutes, the signal for 5-FC had dropped to 50% of its original intensity and the signal for 5-FU had increased to approximately 40% of the original 5-FC signal indicating conversion of 5-FC to 5-FU.

EXAMPLE 27

Optimize the Conditions to Achieve Prolonged Maximal Production of 5-FU in Mouse Tumor Models Monitored by MRS.

MRS was used to optimize the prodrug approach using mouse tumor models. Metastatic hepatic tumor models of colon and pancreatic cancer were developed. Special delivery procedures for adenovirus and the delivery of the prodrug were proposed. Pancreatic and colon tumors were grown both subcutaneously and in the liver following intrasplenic injection and the tumors were transduced with cytosine deaminase containing adenovirus. The adenovirus will be targeted to the tumors in the liver via basic fibroblast growth factor. The animals and tumors will then b e subjected to varying dosing schedules of the prodrug, to varying amounts of radiation and to multiple doses of the adenovirus. MRS allows a continuous in vivo detection system for 5-FU during these treatment conditions in the same animal over time. Through this, each mouse will be monitored over time and the pharmacokinetics measured of the prodrug 5-FC, the active drug 5-FU, along with monitoring which combination of procedures produces the greatest inhibition of tumor growth. It is expected that the use of MRS can help maximize the tumoricidal properties of CD/5-FC gene therapy and that planned human trials will also incorporate MRS into the experimental design and will directly benefit from this improved efficacy.

In vivo model: $2 \times 10^7$ LS174T cells transfected at a MOI of 100 with AdCMVCD were injected into a subcutaneous area in the flank of a nude mouse. Locally, approximately 50 microliters of 3.8 mM 5-FC was injected at the site of the tumor after which these animals were placed in the magnet and evaluated for the presence of 5-FC and the conversion of 5-FC to 5-FU by the adenoviral cytosine deaminase gene. The results demonstrate that the initial time point evaluated was at 10 minutes at which there was a significant peak for 5-FU (FIG. 13). The integral of the 5-FU peak exceeded that of the 5-FC peak for 55 minutes (FIG. 14).

EXAMPLE 28

Correlate the Levels of 5-FU Produced with Therapeutic Outcome in Tumors Treated with Cytosine Deaminase Encoding Adenovirus, 5-FC and Radiation Therapy Therapy studies will be performed oncurrently with the imaging studies described in Example 27. The results obtained will demonstrate the correlation between 5-FU production in the tumor and the therapeutic efficacy of the therapy protocol.

Discussion

The enhancement of gene expression in pancreatic and cholangiocarcinoma cell lines was augmented 10–100 times with the Fab-FGF2 redirected virus, and was blocked by an excess of FGF2 and by free heparin sulfate. As shown by Goldman et al. (39), there was enhancement of cellular transduction mediated by Fab-FGF2 redirection of adenoviral infection in human Kaposi's sarcoma (KS) cells (39). To attempt to distinguish whether the: enhanced luciferase gene expression was due to increased gene expression within each cell, or to enhanced transduction efficiency of the AdCMVCD+Fab-FGF2 conjugated virus, redirection experiments with AdCMVLacZ were performed. In vitro, the transduction efficiency of SK-ChA-1 and BXPC-3 cells was substantially improved by the Fab-FGF2 moiety (FIG. 8), indicating that significantly greater number of cells were transduced with the redirected virus.

An objective of the present invention was to demonstrate that cytosine deaminase mediated cytotoxicity was enhanced by Fab-FGF2 redirection resulting in greater cytotoxicity. At low viral MOIs in SK-ChA-1 and BXPC-3 cells, there was significantly increased cytosine deaminase gene function measured by conversion of 5-FC into 5-FU, and induction of cytotoxicity. The CFPAC-1 cell line did not demonstrate the degree of enhanced 5-FU production or induction of cytotoxicity with redirected AdCMVCD at low MOIs. Cytotoxicity was only seen with the Fab-FGF2 retargeted virus at high viral doses. This has important implications to treatment of in situ tumors in a clinical setting, as the effectiveness of a single vector administration may be substantially improved. The in vivo experiments indicated that in a multimodality therapy model of human pancreatic cancer, the Fab'-FGF2 redirected AdCMVCD resulted in enhanced tumor growth inhibition compared to native virus alone.

These observations have clear importance in clinical gene therapy applications. Methodologies to enhance the therapeutic effect of the first dose of vector are very important, as many studies have shown decreasing effectiveness of repeat adenoviral vector administration. Additionally, limited clinical experience indicates that multi-modality therapy incorporating neoadjuvant 5-FU chemotherapy and radiation therapy may improve treatment for other refractory malignancies (e.g. rectal or rectosigmoid). Improved treatment of established human tumors is a clinically important goal as patients with both cholangiocarcinoma and pancreatic carcinoma generally present with advanced disease, refractory to current treatment. The present invention indicates an improved tumor response to therapy with AdCMVCD+Fab'-FGF2 compared to AdCMVCD alone in combination with 5-FC treatment and external beam radiotherapy.

The results reported herein demonstrate that the retargeted AdCMVCD in conjunction with systemic 5-FC administration and external beam radiotherapy was more efficacious in treating established pancreatic tumors in vivo. Thus, this finding validates the efficacy of FGF2-retargeting with this therapeutic gene and a human interventional trial.

In conclusion, the enhanced gene delivery obtained i n hepatobiliary cancer cells with the Fab-FGF2 redirected adenoviruses translated into enhanced cytotoxicity to pancreatic and cholangiocarcinoma cells utilizing the CD/5-FC toxin gene prodrug system both in vitro and in vivo. These findings provide the rationale for investigating such tropism modified adenoviruses in a clinical setting.

The preliminary data of continuous monitoring conversion of 5-FC to 5-FU via MRS confirm the possibility of detecting the conversion of 5-FC to 5-FU in both an in vitro and in vivo setting. Future studies involves in vivo pancreatic and colon tumor models to evaluate the efficacy of AdCMVCD with and without radiation (5×3 Gy fractions)

in the treatment of pancreatic and colon tumor correlated to the conversion of 5-FC to 5-FU detected by MRS. Conversion studies will for the first time allow the use of a noninvasive method to evaluate the role of gene therapy in the treatment of a lethal tumor by determining intratumoral levels of 5-FU as it is converted from 5-FC via the cytosine deaminase gene. Alternate adenoviral, 5-FC and radiation delivery schedules will be devised based on the data obtained from the initial optimization study. These studies will also provide the basis for development of further subcutaneous and liver metastatic models which will allow for the combined treatment of 5-FU and radiation along with noninvasive detection using MRS. The long term goal of these studies is application to the clinical setting for the detection of intratumoral 5-FU established through molecular chemotherapy.

The following references were cited: herein.
1. Roth & Cristiano, *J. Natl. Cancer Inst.* 89, 21–39, 1997.
2. Rosenberg, et al., *Hum. Gene Ther.* 7, 1621–47, 1996.
3. Yang, et al., *Ann. Surg.* 224, 405–14, 1996.
4. Batra, et al., *J. Biol. Chem.* 272, 11736–43, 1997.
5. Lawrence, T. S., et al., *Semin. Radiat. Oncol.* 7, 247–334, 1997.
6. Hsue, et al., *Int. J. Radiat. Oncol. Biol. Phys.* 34, 445–450, 1996.
7. Oberfield, R. A., et al., *World J. Surg.* 12, 105–108, 1988.
8. Buchsbaum, D. J., et al., *Gene Ther.* 3, 1042–1068, 1996.
9. Weichselbaum, R. R., et al., *Cancer Res.* 54, 4266–4269, 1994.
10. Hallahan, D. E., et al., *Nature Med.* 1, 786–791, 1995.
11. Kim, J. H., et al., *Cancer Res.* 54, 6053–6056, 1994.
12. Kim, et al., *Int. J. Radiat. Oncol. Biol. Phys.* 33, 861–868, 1995.
13. Khil, M. S., et al., *Clin. Cancer Res.* 2, 53–57, 1996.
14. Pederson, L. C., et al., *Cancer Res.* 57, 4325–4332, 1997.
15. Pederson, L. C., et al., *J. Gastrointestinal Surg.* 2, 283–291 1998.
16. Gallardo, D., et al., *Cancer Res.* 56, 4891–4893, 1996.
17. Spitz, F. R., et al., *Clin. Cancer Res.* 2, 1665–1671, 1996.
18. Raben, D., et al., *Cancer Gene Ther.* 2, 330, 1995.
19. Raben, D., et al., *Gene Ther.* 3, 567–580, 1996.
20. Rogers, B. E., et al., *J. Nucl. Med.* 38, 1221–1229, 1997.
21. Rosenfeld, M. E., et al., *Clin. Cancer Res.* 3, 1187–1194, 1997.
22. Austin, E. A., et al., *Mol. Pharmacol.* 43, 380–387, 1993.
23. Hamstra, et al., *Human Gene Therapy* 10, 1993–2003, 1999.
24. Huber, B. E., et al., *Cancer Res.* 53, 4619–4626, 1993.
25. Dong, Y., et al., *Human Gene Ther.* 7, 713–720, 1996.
26. Hirschowitz, E. A., et al., *Hum. Gene Ther.* 6, 1055–1063, 1995.
27. Rogulski, K. R., et al., *Human Gene Ther.* 8, 73–85, 1997.
28. Becker, T. C., et al., *Meth. Cell Biol.* 43, 161–189, 1994.
29. Ohwada, A., et al., *Human Gene Ther.* 7, 1567–1576, 1996.
30. Saunders, K., et al., *Am. Surg.* 57, 816–820, 1991.
31. Vauthey, J. -N., et al., *Semin. Liver Dis.* 14, 109–114, 1994.
32. Denning, C., et al., *Human Gene Ther.* 8, 1825–1835, 1997.
33. Paillard, F., *Human Gene Ther.* 8, 1733–1736, 1997.
34. Sosnowski et al., *J. Biol. Chem.* 271, 33647–53, 1996.
35. Rosenfeld et al., *Clin. Cancer Res.* 1, 1571–1580, 1995.
36. Towbin et al., *PNAS* 76, 4350–4354, 1979.
37. Haack, et al., *Human Gene Therapy* 8, 1395–401, 1997.
38. Haberkorn et al., *J. Nucl. Med.* 37, 87–94, 1996.
39. Goldman, *Cancer Research* 57, 1447–1451, 1997.
40. Kievit, E., et al., *Cancer Research* 59, 1417–1421, 1999.
41. Aboagye, et al., *Cancer Research* 58, 4075–4078, 1998.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating an individual having a solid tumor, wherein cells comprising said tumor are capable of infection by an adenovirus encoding a cytosine deaminase gene, said tumor cells further capable of expressing said gene, comprising the steps of:

treating said individual with the adenovirus encoding said cytosine deaminase gene;

administering a dose of 5-fluorocytosine to said individual, said 5-fluorocytosine administered at about 400 mg/kg to about 500 mg/kg twice per day; and treating said individual with a single fraction of radiation wherein said single fraction is a daily dose of about 2 Gy to about 3 Gy administered over a 4 to 6 week period; or treating said individual with multiple fractions of radiation wherein said multiple fractions are a three fraction dose of 5 Gy or a five fraction dose of 2 Gy.

2. The method of claim 1, wherein said tumor is selected from the group consisting of colon cancer, pancreatic cancer, prostate cancer, lung cancer, brain cancer, head and neck cancer and cholangiocarcinoma.

3. The method of claim 1, wherein said adenovirus is under control of a tumor specific promoter.

4. The method of claim 3, wherein said promoter is selected from the group consisting of a carcinoembryonic antigen promoter, DF3/MUC1 promoter, a prostate specific antigen promoter, surfactant protein A promoter, leukoprotease inhibitor promoter, erbB-2 promoter, alpha fetoprotein promoter and E2F promoter.

5. The method of claim 1, wherein said cytosine deaminase gene is *E. coli* cytosine deaminase gene.

6. The method of claim 1, wherein said 5-fluorocytosine is administered in a dosage of about 400 mg/kg twice per day.

7. The method of claim 1, wherein said radiation is administered via brachytherapy.

* * * * *